(12) United States Patent
Kirsten et al.

(10) Patent No.: US 6,420,313 B1
(45) Date of Patent: Jul. 16, 2002

(54) THIENYLALKYLAMINO-1,3,5-TRIAZINES AND THE USE THEREOF AS HERBICIDES

(75) Inventors: Rolf Kirsten, Monheim; Hans-Jochem Riebel, Selters; Stefan Lehr, Langenfeld; Katharina Voigt; Kristian Kather, both of Monheim; Mark Wilhelm Drewes, Langenfeld, all of (DE); Markus Dollinger, Overland Park, KS (US); Ingo Wetcholowsky, Vinhedo (BR); Yukiyoshi Watanabe, Oyama; Toshio Goto, Kokubunji-machi, both of (JP)

(73) Assignees: Bayer Aktiengesellschaft, Leverkusen (DE); Nihon Bayer Agrochem, K.K., Tokyo (JP)

( * ) Notice: Subject to any disclaimer, the term of this patent is extended or adjusted under 35 U.S.C. 154(b) by 0 days.

(21) Appl. No.: 09/647,655

(22) PCT Filed: Mar. 26, 1999

(86) PCT No.: PCT/EP99/02089

§ 371 (c)(1), (2), (4) Date: Nov. 30, 2000

(87) PCT Pub. No.: WO99/52904

PCT Pub. Date: Oct. 21, 1999

(30) Foreign Application Priority Data

Apr. 9, 1998 (DE) ......................... 198 16 055

(51) Int. Cl.[7] ............... C07D 251/18; C07D 251/50; A01N 43/70
(52) U.S. Cl. ................ 504/230; 544/207; 544/209
(58) Field of Search ............... 544/209, 207; 504/232, 233, 230

(56) References Cited

U.S. PATENT DOCUMENTS 3,816,419 A   6/1974   Cross et al. ............. 260/249.9

FOREIGN PATENT DOCUMENTS

| DE | 2115318 | 12/1971 |
|---|---|---|
| JP | 62-222166 | 9/1998 |
| WO | 97/08156 | 3/1997 |
| WO | 98/15537 | 4/1998 |
| WO | 98/15538 | 4/1998 |
| WO | 98/15539 | 4/1998 |
| WO | 99/19309 | 4/1999 |

OTHER PUBLICATIONS

Database WPI, Section Ch, Week 8843, Derwent Publication Ltd., London, GB; Class C02, AN 88–303295 XP002111262–& JP 63 222166 A (IDEMITSU KOSAN CO LTD.), Sep. 16, 1988.

*Primary Examiner*—John M. Ford
(74) *Attorney, Agent, or Firm*—Joseph C. Gil; John E. Mrozinski, Jr.

(57) ABSTRACT

The invention relates to novel thienylalkylamino-1,3,5-triazines of the general formula (I)

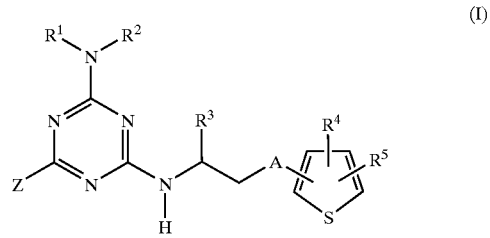

in which A, $R^1$, $R^2$, $R^3$, $R^4$, $R^5$ and Z are as defined in the description, to processes for their preparation, to their use as herbicides and to novel intermediates and their preparation.

13 Claims, No Drawings

THIENYLALKYLAMINO-1,3,5-TRIAZINES AND THE USE THEREOF AS HERBICIDES

This is a 371 National Application of of PCT/EP99/02089, filed Mar. 26, 1999.

The invention relates to novel thienylalkylamino-1,3,5-triazines, to processes for their preparation and to their use as herbicides.

A number of thienylalkylaminotriazines are already known from the (patent) literature (cf. JP 63222166—cited in Chem. Abstracts 111:97288w). However, these compounds have hitherto not attained any particular importance.

This invention, accordingly, provides the novel thienylalkylamino-1,3,5-triazines of the general formula (I)

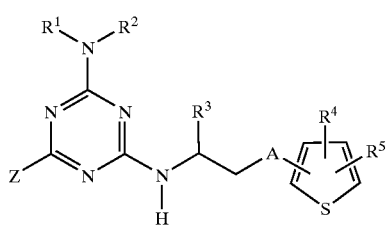

(I)

in which
- A represents methylene (—$CH_2$—) or dimethylene (—$CH_2CH_2$—),
- $R^1$ represents hydrogen or represents optionally cyano-, halogen- or $C_1$–$C_4$-alkoxy-substituted alkyl having 1 to 4 carbon atoms,
- $R^2$ represents hydrogen, represents formyl or represents in each case optionally cyano-, halogen- or $C_1$–$C_4$-alkoxy-substituted alkyl, alkylcarbonyl, alkoxycarbonyl or alkylaminocarbonyl having in each case 1 to 4 carbon atoms in the alkyl groups,
- $R^3$ represents hydrogen or represents optionally cyano-, halogen- or $C_1$–$C_4$-alkoxy-substituted alkyl having 1 to 4 carbon atoms or represents optionally cyano-, halogen- or $C_1$–$C_4$-alkyl-substituted cycloalkyl having 3 to 6 carbon atoms,
- $R^4$ represents nitro, cyano, carbamoyl, thiocarbamoyl, halogen, represents in each case optionally halogen-substituted alkyl, alkoxy, alkylcarbonyl or alkoxycarbonyl having in each case up to 4 carbon atoms, or—in the case that A represents dimethylene—also represents hydrogen,
- $R^5$ represents hydrogen, halogen or represents in each case optionally halogen-substituted alkyl or alkoxy having in each case 1 to 4 carbon atoms, and
- Z represents hydrogen, represents halogen, represents in each case optionally cyano-, halogen-, hydroxyl-, $C_1$–$C_4$-alkoxy- or $C_1$–$C_4$-alkylthio-substituted alkyl or alkoxy having in each case 1 to 6 carbon atoms, represents in each case optionally cyano-, halogen- or $C_1$–$C_4$-alkoxy-substituted alkylcarbonyl, alkoxycarbonyl, alkylthio, alkylsulphinyl or alkylsulphonyl having in each case 1 to 6 carbon atoms in the alkyl groups, represents in each case optionally halogen-substituted alkenyl or alkinyl having 2 to 6 carbon atoms, or represents optionally cyano-, halogen- or $C_1$–$C_4$-alkyl-substituted cyclo-alkyl having 3 to 6 carbon atoms.

The novel thienylalkylaminotriazines of the general formula (I) are obtained when (a) biguanides of the general formula (II)

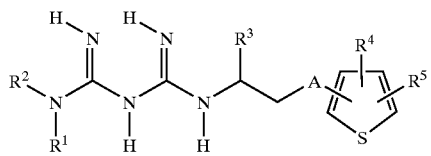

(II)

in which
A, $R^1$, $R^2$, $R^3$, $R^4$ and $R^5$ are as defined above
and/or acid adducts of compounds of the general formula (II)—are reacted with alkoxycarbonyl compounds of the general formula (III)

Z—CO—OR' (III)

in which
Z is as defined above and
R' represents alkyl,
if appropriate in the presence of a reaction auxiliary and
if appropriate in the presence of a diluent,
or when
(b) substituted halogenotriazines of the general formula (IV)

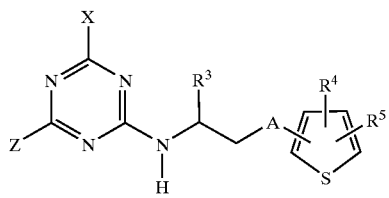

(IV)

in which
A, $R^3$, $R^4$, $R^5$ and Z are as defined above and
X represents halogen,
are reacted with nitrogen compounds of the general formula (V)

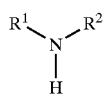

(V)

in which
$R^1$ and $R^2$ are as defined above,
if appropriate in the presence of a reaction auxiliary and
if appropriate in the presence of a diluent,
or when
(c) substituted aminotriazines of the general formula (VI)

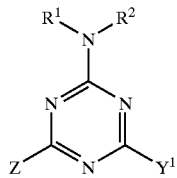

(VI)

in which
R¹, R² and Z are as defined above and
Y¹ represents halogen or alkoxy,
are reacted with substituted alkylamines of the general formula (VII)

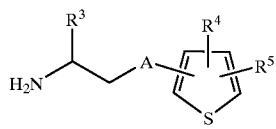
(VII)

in which
A, R³, R⁴ and R⁵ are as defined above,
if appropriate in the presence of a reaction auxiliary and
if appropriate in the presence of a diluent,
or when
(d) substituted 2,4-diamino-1,3,5-triazines of the general formula (Ia)

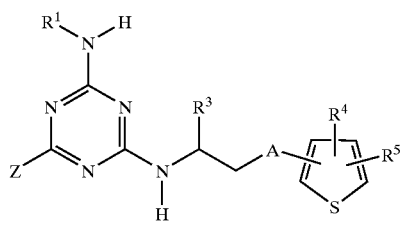
(Ia)

in which
A, R¹, R³, R⁴, R⁵ and Z are as defined above,
are reacted with alkylating or acylating agents of the general formula (VIII)

Y²—R² (VIII)

in which
R² is as defined above, except for hydrogen, and
Y² represents halogen, —O—R² or —O—CO—R²,
if appropriate in the presence of a reaction auxiliary and
if appropriate in the presence of a diluent,
and, if appropriate, further conversions within the scope of the above definition of substituents are carried out by customary methods on the compounds of the general formula (I) obtained according to the processes described under (a), (b), (c) or (d).

The novel substituted 2,4-diamino-1,3,5-triazines of the general formula (I) have strong and selective herbicidal activity.

If appropriate, the compounds of the general formula (I) according to the invention contain an asymmetrically substituted carbon atom and can therefore be present in different enantiomeric (R- and S-configured forms) and/or diastereomeric forms. The invention relates both to the various possible individual enantiomeric or stereo-isomeric forms of the compounds of the general formula (I), and to the mixtures of these isomeric compounds.

In the definitions, the hydrocarbon chains, such as alkyl, are in each case straight-chain or branched, including in combination with hetero atoms, such as in alkoxy or alkylthio.

Halogen generally represents fluorine, chlorine, bromine or iodine, preferably fluorine, chlorine or bromine, in particular fluorine or chlorine.

The invention preferably provides compounds of the formula (I) in which

A represents methylene (—CH₂—) or dimethylene (—CH₂CH₂—),

R¹ represents hydrogen or represents in each case optionally cyano-, fluorine-, chlorine-, methoxy- or ethoxy-substituted methyl, ethyl, n- or i-propyl, R² represents hydrogen, represents formyl or represents in each case optionally cyano-, fluorine-, chlorine-, methoxy- or ethoxy-substituted methyl, ethyl, n- or i-propyl, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, R³ represents hydrogen or represents in each case optionally cyano-, fluorine-, chlorine-, methoxy- or ethoxy-substituted methyl, ethyl, n- or i-propyl, or represents in each case optionally cyano-, fluorine-, chlorine-, methyl- or ethyl-substituted cyclopropyl, cyclobutyl, cyclopentyl or cyclohexyl, R⁴ represents nitro, cyano, carbamoyl, thiocarbamoyl, fluorine, chlorine, bromine, or represents in each case optionally fluorine- and/or chlorine-substituted methyl, ethyl, n- or i-propyl, methoxy, ethoxy, n- or i-propoxy and—in the case that A represents dimethylene—also represents hydrogen, R⁵ represents hydrogen, fluorine, chlorine, bromine, or represents in each case optionally fluorine- and/or chlorine-substituted methyl, ethyl, n- or i-propyl, methoxy, ethoxy, n- or i-propoxy, and Z represents hydrogen, represents fluorine, chlorine, bromine, represents in each case optionally cyano-, fluorine-, chlorine-, bromine-, hydroxyl-, methoxy-, ethoxy-, methylthio- or ethylthio-substituted methyl, ethyl, n- or i-propyl, n-, i-, s- or t-butyl, methoxy, ethoxy, n- or i-propoxy, n-, i-, s- or t-butoxy, represents in each case optionally cyano-, fluorine-, chlorine-, methoxy- or ethoxy-substituted acetyl, propionyl, n- or i-butyroyl, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents in each case optionally fluorine-, chlorine- and/or bromine-substituted ethenyl, propenyl butenyl, ethinyl, propinyl or butinyl, or represents optionally cyano-, fluorine-, chlorine-, bromine-, methyl- or ethyl-substituted cyclopropyl, cyclobutyl, cyclopentyl or cyclohexyl.

The invention relates in particular to compounds of the formula (I) in which

A represents methylene (—CH₂—) or dimethylene (—CH₂CH₂—),

R¹ represents hydrogen,

R² represents hydrogen, formyl, acetyl, propionyl, n- or i-butyroyl, methoxycarbonyl, ethoxycarbonyl, n- or i-propoxycarbonyl, R³ represents methyl, ethyl, n- or i-propyl, R⁴ represents nitro, cyano, fluorine, chlorine, bromine, or represents in each case optionally fluorine- and/or chlorine-substituted methyl, ethyl, n- or i-propyl, methoxy, ethoxy, n- or i-propoxy and—in the case that A represents dimethylene—also represents hydrogen, R⁵ represents hydrogen, fluorine, chlorine, bromine, or represents in each case optionally fluorine- and/or chlorine-substituted methyl, ethyl, n- or i-propyl, methoxy, ethoxy, n- or i-propoxy, and Z represents in each case optionally fluorine-, chlorine-, methoxy- or ethoxy-substituted methyl, ethyl, n- or i-propyl, or represents cyclopropyl.

A very particularly preferred group are the compounds of the formula (I) in which A represents methylene and $R^1$, $R^2$, $R^3$, $R^4$, $R^5$ and Z have the meaning given above as being particularly preferred. Particular emphasis is given here to the R enantiomers and S enantiomers which are possible in each case. Particular emphasis is furthermore given to the compounds in which Z represents 1-fluoroethyl and 1-fluoro-1-methyl-ethyl.

A further very particularly preferred group are the compounds of the formula (I) in which A represents dimethylene and $R^1$, $R^2$, $R^3$, $R^4$, $R^5$ and Z have the meaning given above as being particularly preferred.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Examples of the compounds of the general formula (I) according to the invention are listed in the groups below.

Group 1

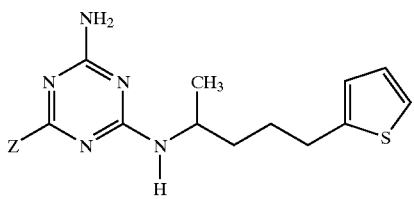

Z has here, for example, the meanings given in the list below:

methyl, ethyl, n- or i-propyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloro-ethyl, 1-bromo-ethyl, 1-chloro-1-fluoro-ethyl, 1-fluoro-propyl, 2-fluoro-propyl, 3-fluoro-propyl, 1-chloro-propyl, 2-chloro-propyl, 3-chloro-propyl, 1-bromo-propyl, 1-fluoro-1-methyl-ethyl, 2-fluoro-1-methyl-ethyl, 1-chloro-1-methyl-ethyl, 2-chloro-1-methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoro-ethyl, 1,1-difluoro-propyl, 1,1-dichloro-propyl, perfluoropropyl, 1-hydroxy-ethyl, 1-hydroxy-1-methyl-ethyl, 1-hydroxy-propyl, methoxymethyl, ethoxymethyl, dimethoxy-methyl, 1-methoxyethyl, 2-methoxy-ethyl, 1,1-dimethoxy-ethyl, 1-ethoxy-ethyl, 2-ethoxy-ethyl, 2,2-dimethoxy-ethyl, 2,2-diethoxy-ethyl, 2-methoxy-1-methyl-ethyl, 2-ethoxy-1-methyl-ethyl, 2,2-bis-methoxy-methyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl.

Group 2

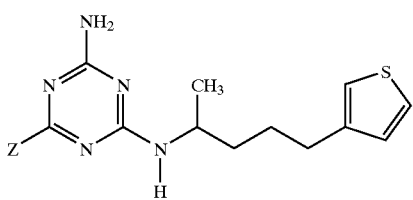

Z has here, for example, the meanings given above in Group 1.

Group 3

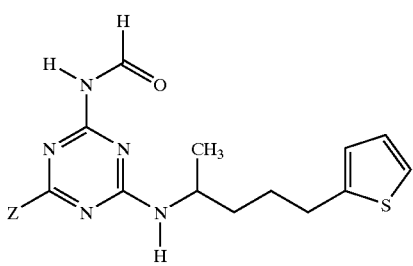

Z has here, for example, the meanings given above in Group 1.

Group 4

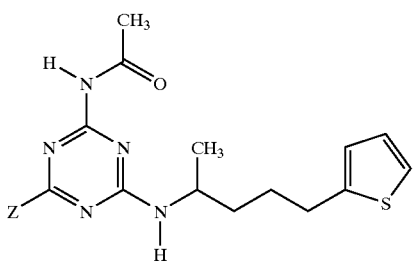

Z has here, for example, the meanings given above in Group 1.

Group 5

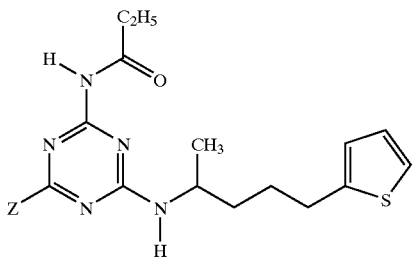

Z has here, for example, the meanings given above in Group 1.

Group 6

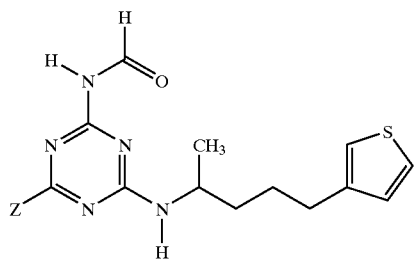

Z has here, for example, the meanings given above in Group 1.

Group 7

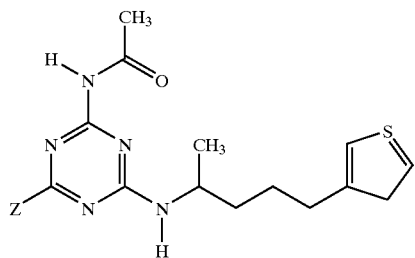

Z has here, for example, the meanings given above in Group 1.

Group 8

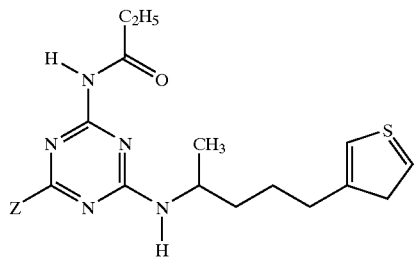

Z has here, for example, the meanings given above in Group 1.

Group 9

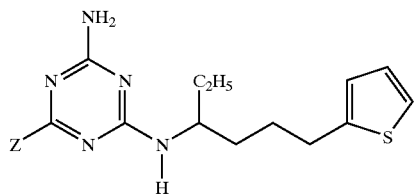

Z has here, for example, the meanings given above in Group 1.

Group 10

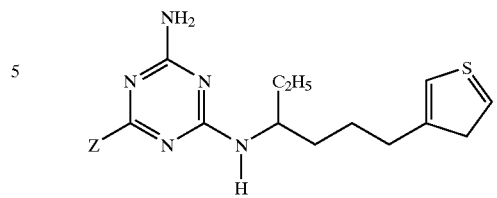

Z has here, for example, the meanings given above in Group 1.

Group 11

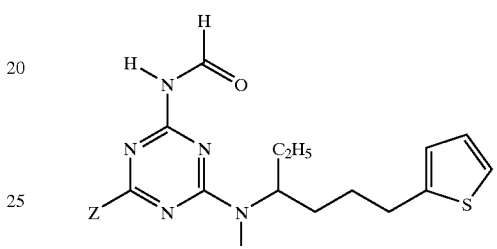

Z has here, for example, the meanings given above in Group 1.

Group 12

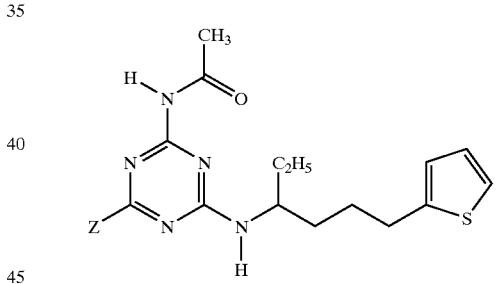

Z has here, for example, the meanings given above in Group 1.

Group 13

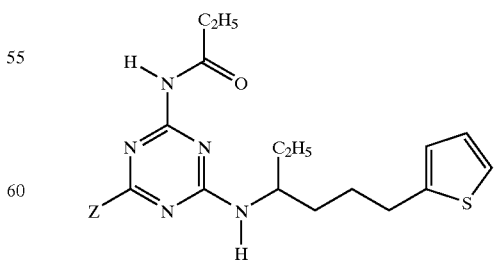

Z has here, for example, the meanings given above in Group 1.

Group 14

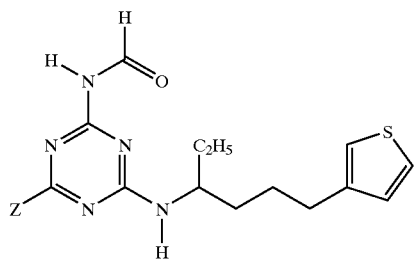

Z has here, for example, the meanings given above in Group 1.

Group 15

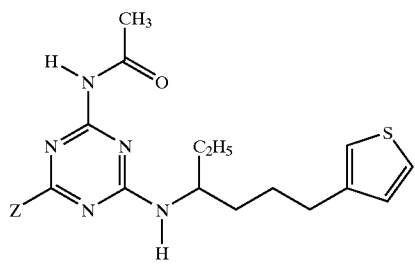

Z has here, for example, the meanings given above in Group 1.

Group 16

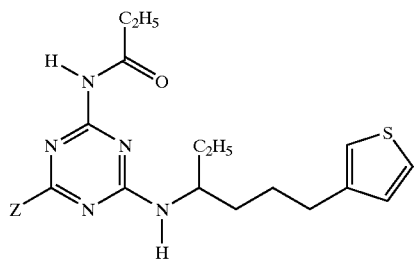

Z has here, for example, the meanings given above in Group 1.

Group 17

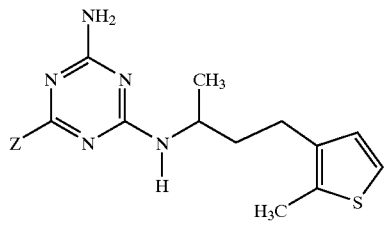

Z has here, for example, the meanings given above in Group 1.

Group 18

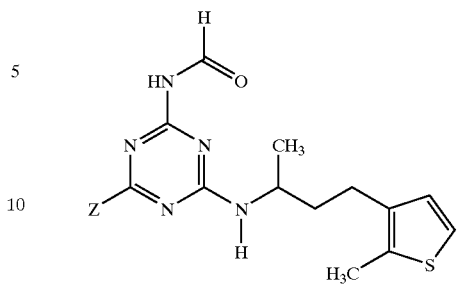

Z has here, for example, the meanings given above in Group 1.

Group 19

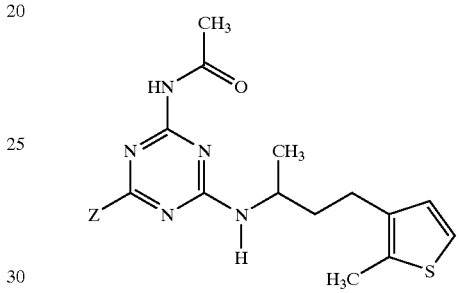

Z has here, for example, the meanings given above in Group 1.

Group 20

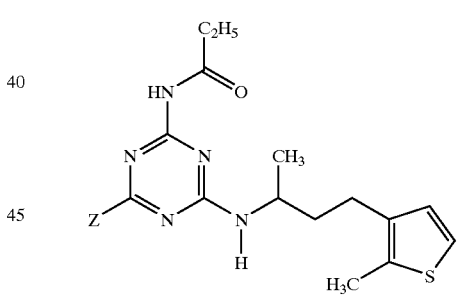

Z has here, for example, the meanings given above in Group 1.

Group 21

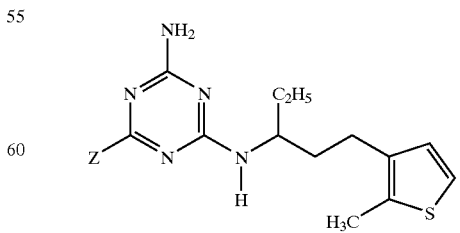

Z has here, for example, the meanings given above in Group 1.

Group 22

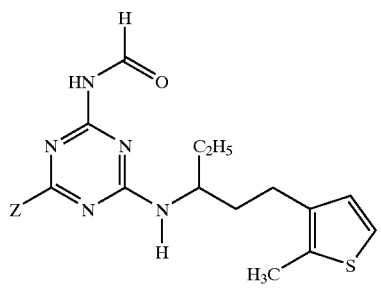

Z has here, for example, the meanings given above in Group 1.

Group 23

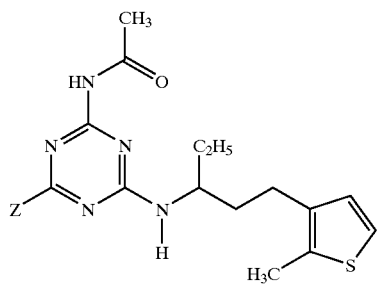

Z has here, for example, the meanings given above in Group 1.

Group 24

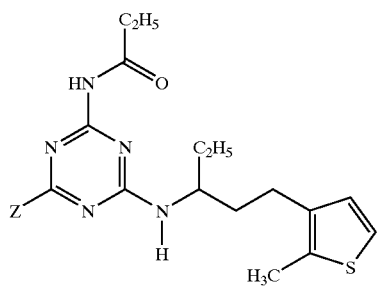

Z has here, for example, the meanings given above in Group 1.

Group 25

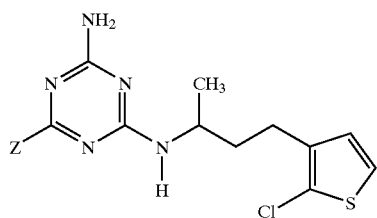

Z has here, for example, the meanings given above in Group 1.

Group 26

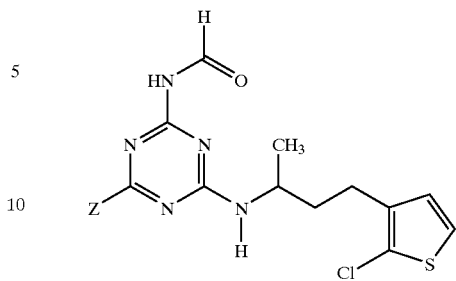

Z has here, for example, the meanings given above in Group 1.

Group 27

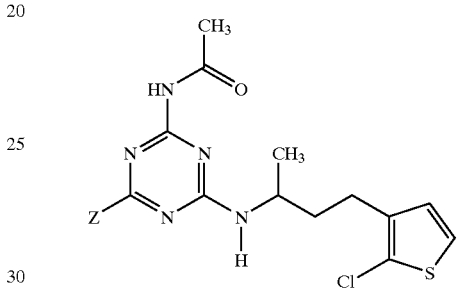

Z has here, for example, the meanings given above in Group 1.

Group 28

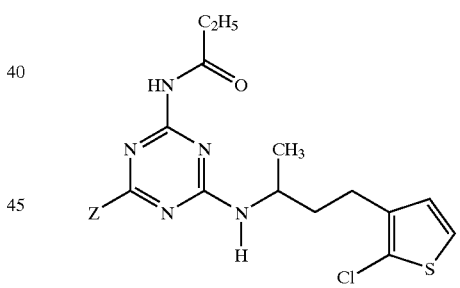

Z has here, for example, the meanings given above in Group 1.

Group 29

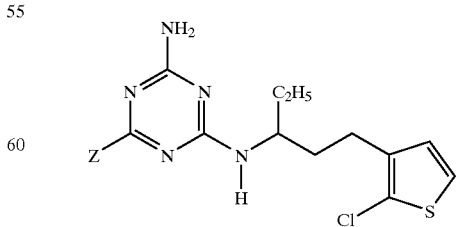

Z has here, for example, the meanings given above in Group 1.

Group 30

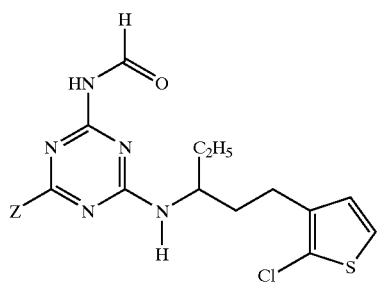

Z has here, for example, the meanings given above in Group 1.

Group 31

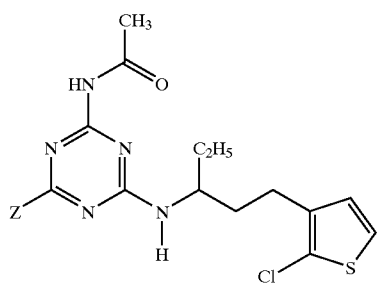

Z has here, for example, the meanings given above in Group 1.

Group 32

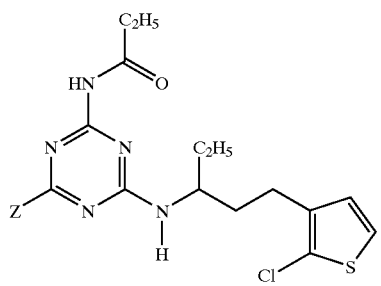

Z has here, for example, the meanings given above in Group 1.

Group 33

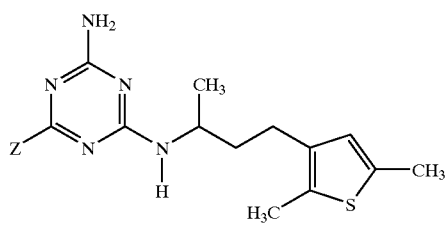

Z has here, for example, the meanings given above in Group 1.

Group 34

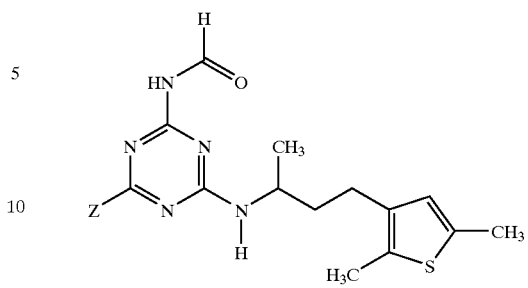

Z has here, for example, the meanings given above in Group 1.

Group 35

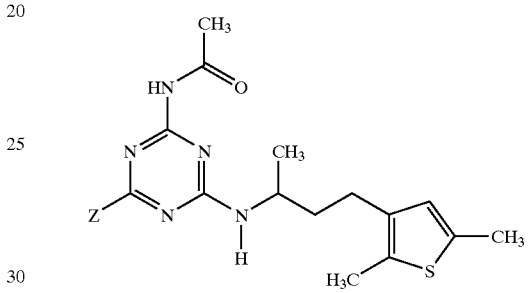

Z has here, for example, the meanings given above in Group 1.

Group 36

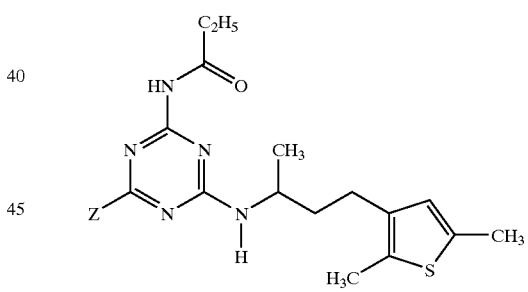

Z has here, for example, the meanings given above in Group 1.

Group 37

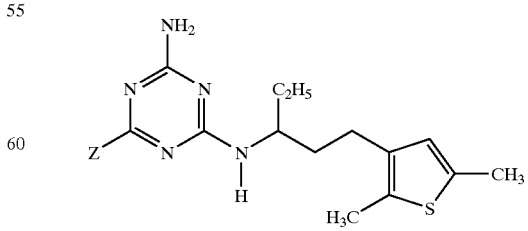

Z has here, for example, the meanings given above in Group 1.

Group 38

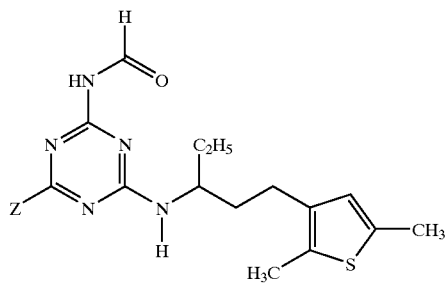

Z has here, for example, the meanings given above in Group 1.

Group 39

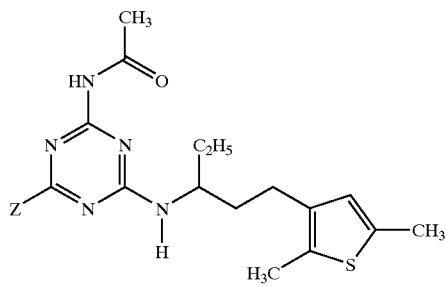

Z has here, for example, the meanings given above in Group 1.

Group 40

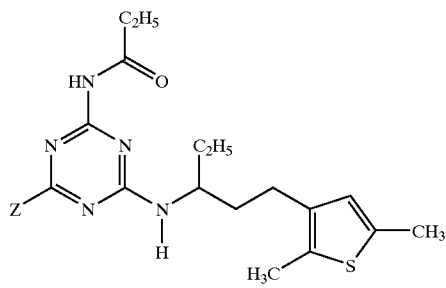

Z has here, for example, the meanings given above in Group 1.

Group 41

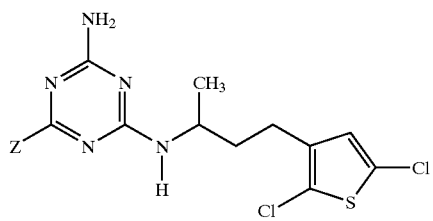

Z has here, for example, the meanings given above in Group 1.

Group 42

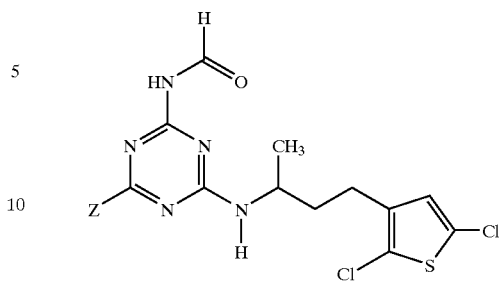

Z has here, for example, the meanings given above in Group 1.

Group 43

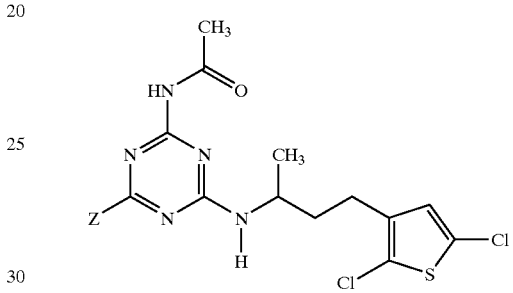

Z has here, for example, the meanings given above in Group 1.

Group 44

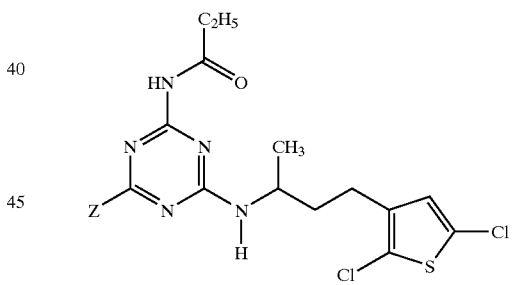

Z has here, for example, the meanings given above in Group 1.

Group 45

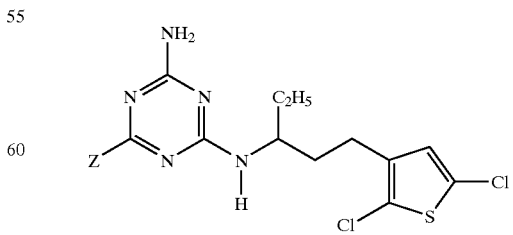

Z has here, for example, the meanings given above in Group 1.

Group 46

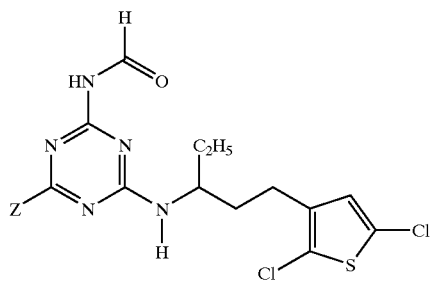

Z has here, for example, the meanings given above in Group 1.

Group 47

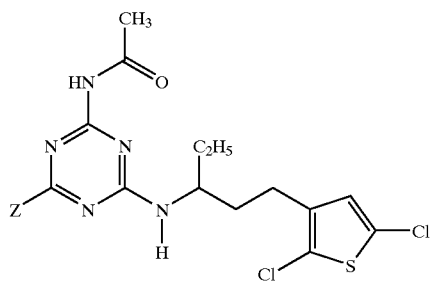

Z has here, for example, the meanings given above in Group 1.

Group 48

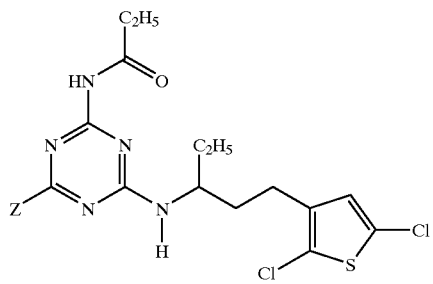

Z has here, for example, the meanings given above in Group 1.

Group 49

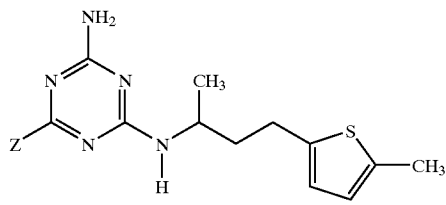

Z has here, for example, the meanings given above in Group 1.

Group 50

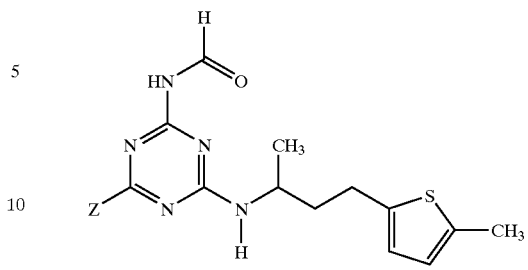

Z has here, for example, the meanings given above in Group 1.

Group 51

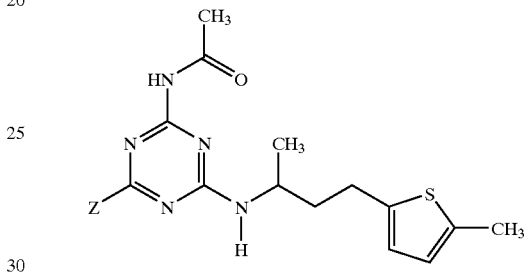

Z has here, for example, the meanings given above in Group 1.

Group 52

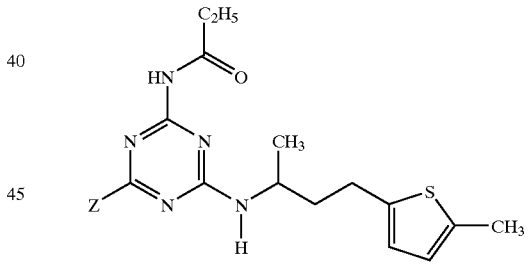

Z has here, for example, the meanings given above in Group 1.

Group 53

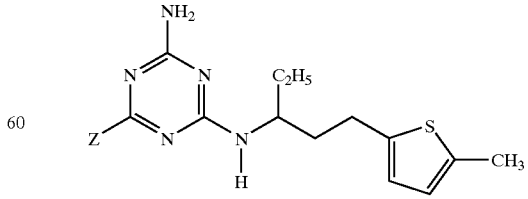

Z has here, for example, the meanings given above in Group 1.

Group 54

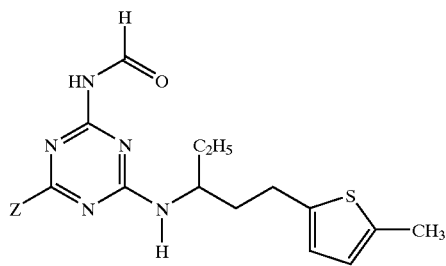

Z has here, for example, the meanings given above in Group 1.

Group 55

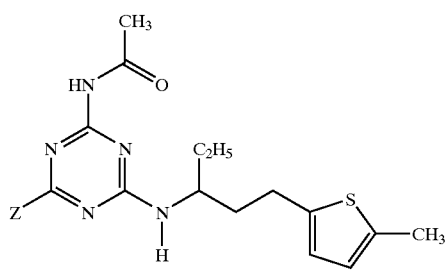

Z has here, for example, the meanings given above in Group 1.

Group 56

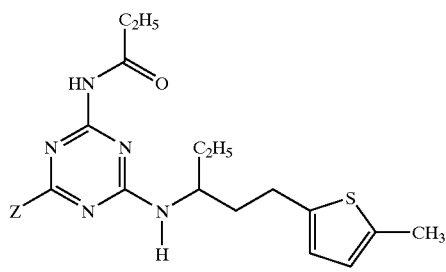

Z has here, for example, the meanings given above in Group 1.

Group 57

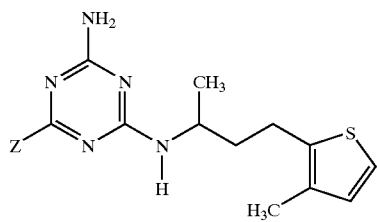

Z has here, for example, the meanings given above in Group 1.

Group 58

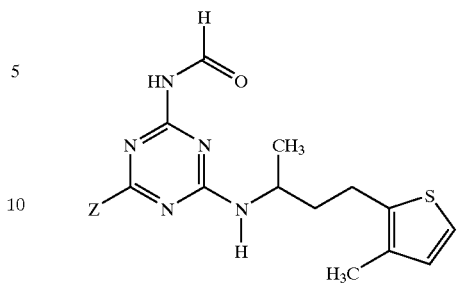

Z has here, for example, the meanings given above in Group 1.

Group 59

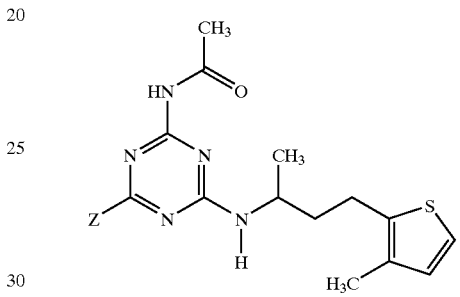

Z has here, for example, the meanings given above in Group 1.

Group 60

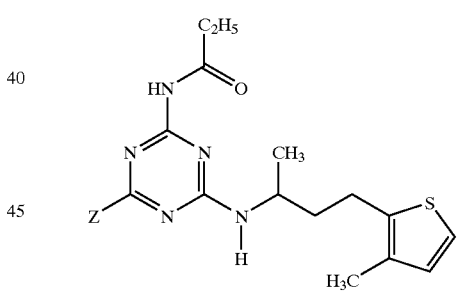

Z has here, for example, the meanings given above in Group 1.

Group 61

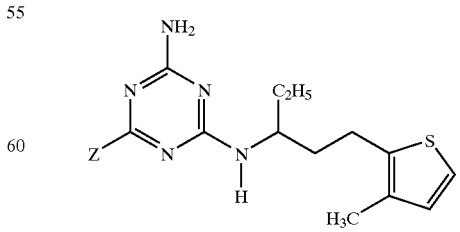

Z has here, for example, the meanings given above in Group 1.

Group 62

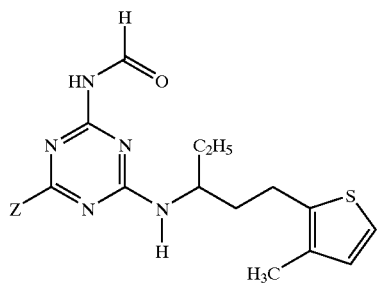

Z has here, for example, the meanings given above in Group 1.

Group 63

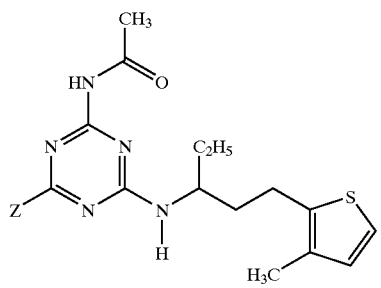

Z has here, for example, the meanings given above in Group 1.

Group 64

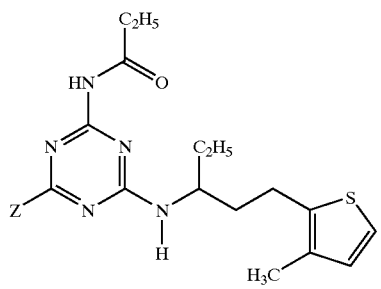

Z has here, for example, the meanings given above in Group 1.

Group 65

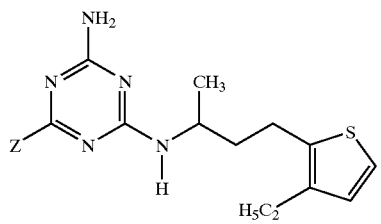

Z has here, for example, the meanings given above in Group 1.

Group 66

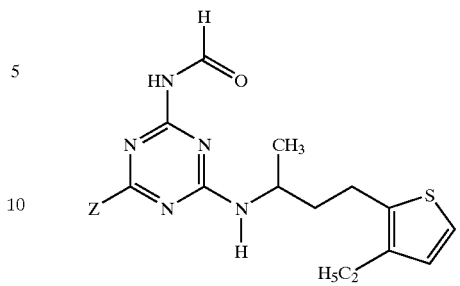

Z has here, for example, the meanings given above in Group 1.

Group 67

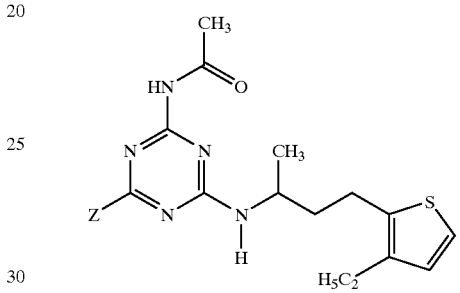

Z has here, for example, the meanings given above in Group 1.

Group 68

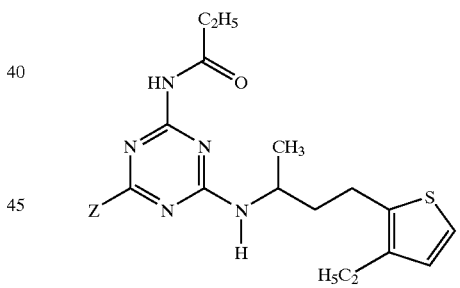

Z has here, for example, the meanings given above in Group 1.

Group 69

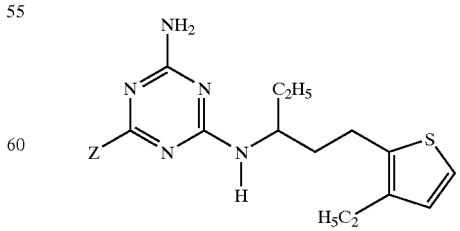

Z has here, for example, the meanings given above in Group 1.

Group 70

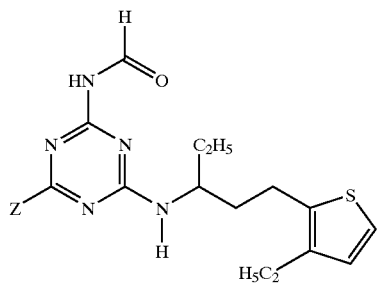

Z has here, for example, the meanings given above in Group 1.

Group 71

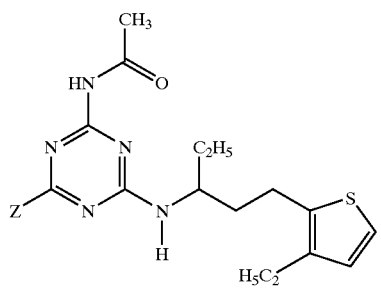

Z has here, for example, the meanings given above in Group 1.

Group 72

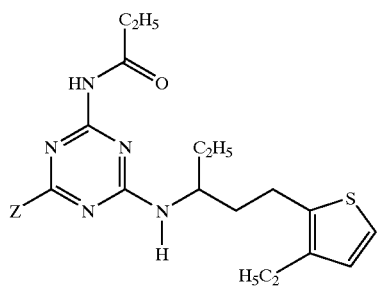

Z has here, for example, the meanings given above in Group 1.

Group 73

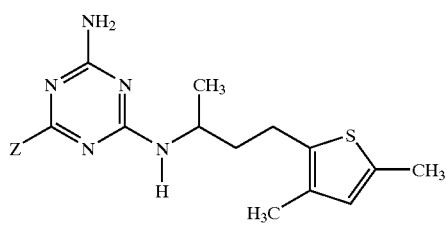

Z has here, for example, the meanings given above in Group 1.

Group 74

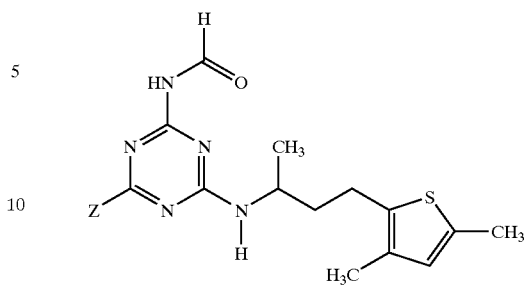

Z has here, for example, the meanings given above in Group 1.

Group 75

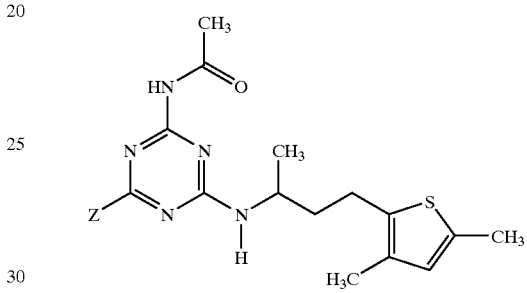

Z has here, for example, the meanings given above in Group 1.

Group 76

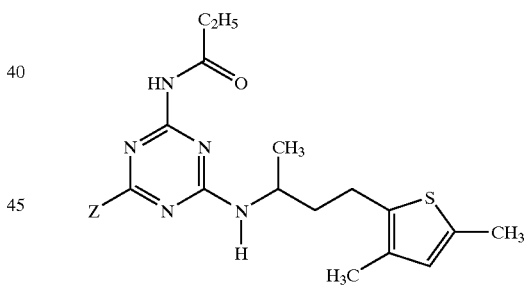

Z has here, for example, the meanings given above in Group 1.

Group 77

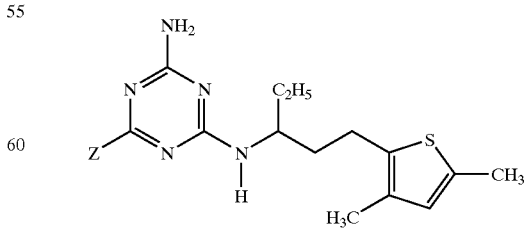

Z has here, for example, the meanings given above in Group 1.

Group 78

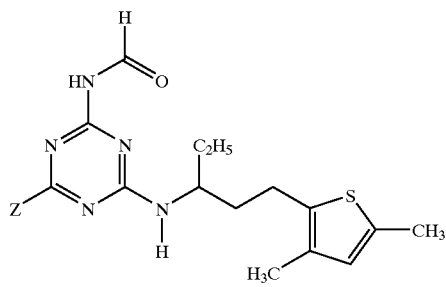

Z has here, for example, the meanings given above in Group 1.

Group 79

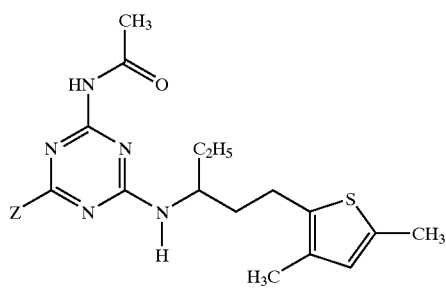

Z has here, for example, the meanings given above in Group 1.

Group 80

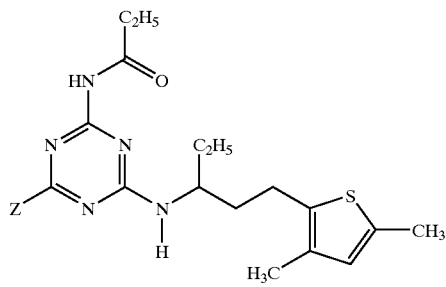

Z has here, for example, the meanings given above in Group 1.

Group 81

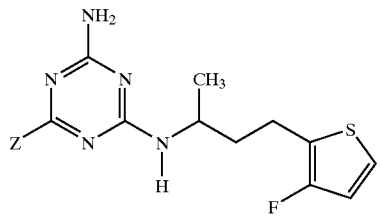

Z has here, for example, the meanings given above in Group 1.

Group 82

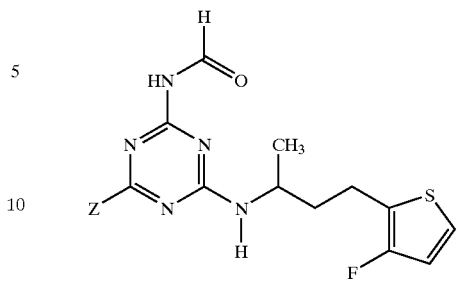

Z has here, for example, the meanings given above in Group 1.

Group 83

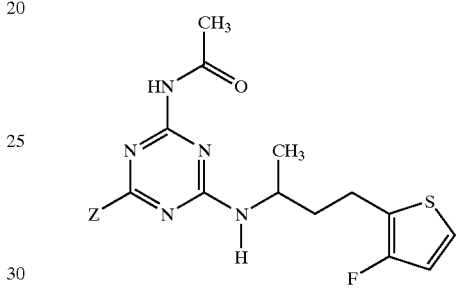

Z has here, for example, the meanings given above in Group 1.

Group 84

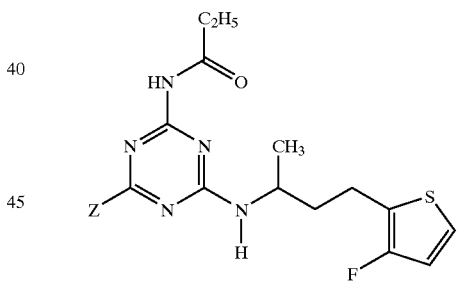

Z has here, for example, the meanings given above in Group 1.

Group 85

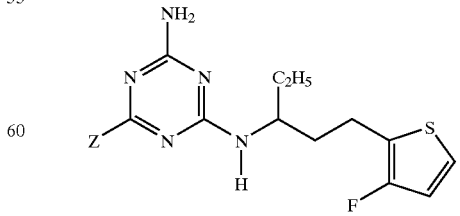

Z has here, for example, the meanings given above in Group 1.

Group 86

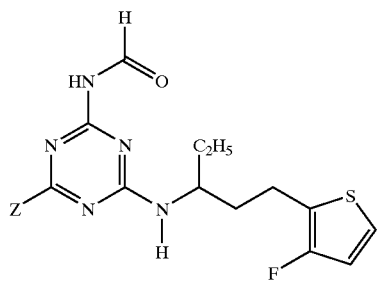

Z has here, for example, the meanings given above in Group 1.

Group 87

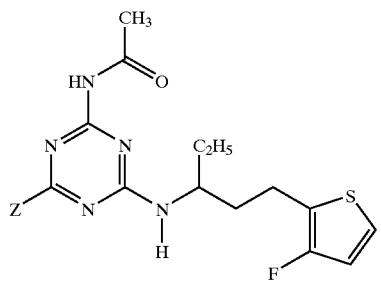

Z has here, for example, the meanings given above in Group 1.

Group 88

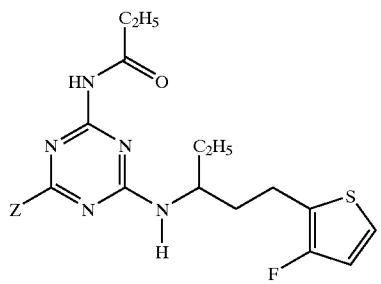

Z has here, for example, the meanings given above in Group 1.

Group 89

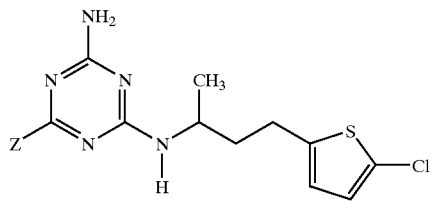

Z has here, for example, the meanings given above in Group 1.

Group 90

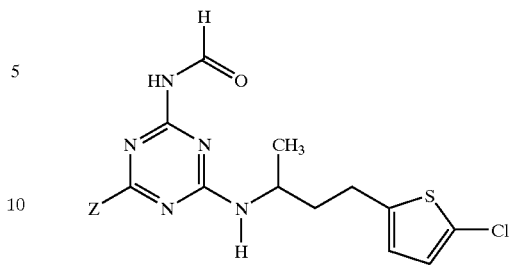

Z has here, for example, the meanings given above in Group 1.

Group 91

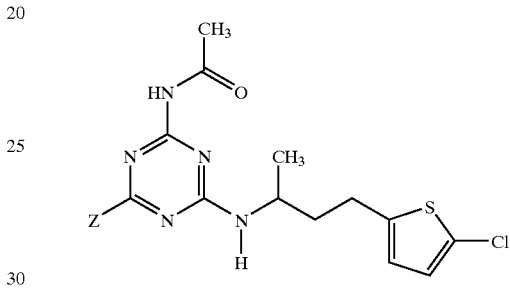

Z has here, for example, the meanings given above in Group 1.

Group 92

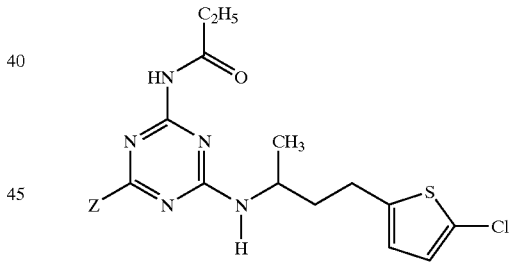

Z has here, for example, the meanings given above in Group 1.

Group 93

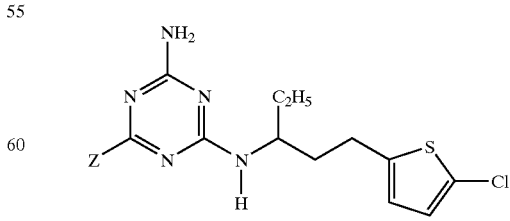

Z has here, for example, the meanings given above in Group 1.

Group 94

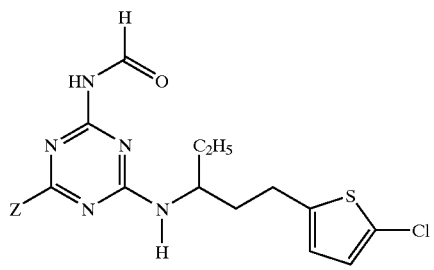

Z has here, for example, the meanings given above in Group 1.

Group 95

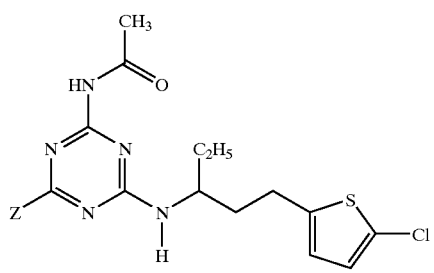

Z has here, for example, the meanings given above in Group 1.

Group 96

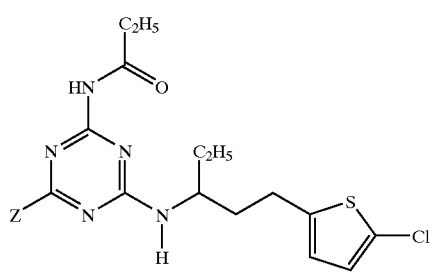

Z has here, for example, the meanings given above in Group 1.

Group 97

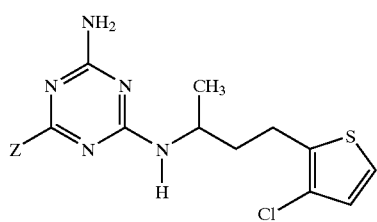

Z has here, for example, the meanings given above in Group 1.

Group 98

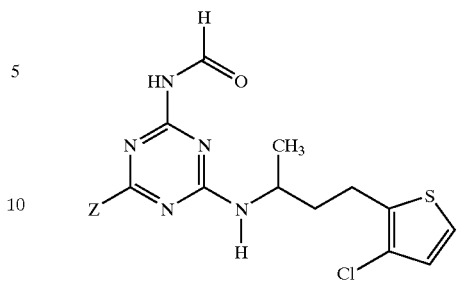

Z has here, for example, the meanings given above in Group 1.

Group 99

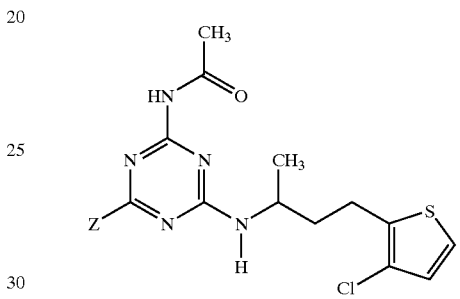

Z has here, for example, the meanings given above in Group 1.

Group 100

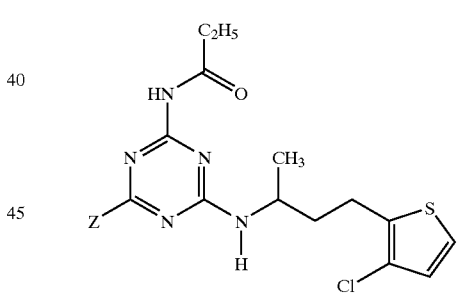

Z has here, for example, the meanings given above in Group 1.

Group 101

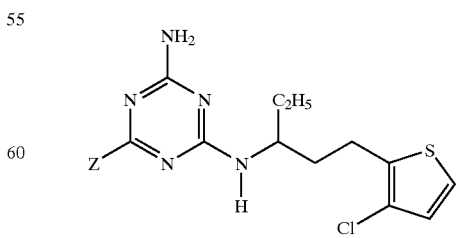

Z has here, for example, the meanings given above in Group 1.

Group 102

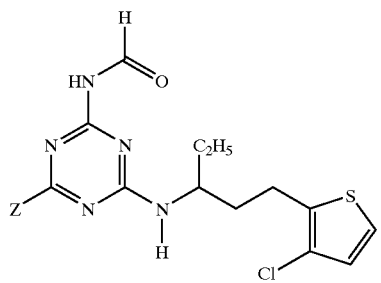

Z has here, for example, the meanings given above in Group 1.

Group 103

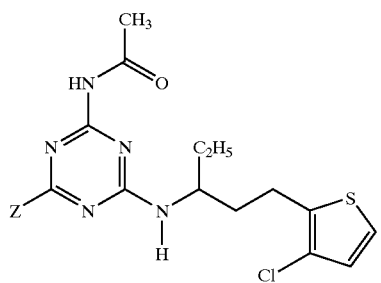

Z has here, for example, the meanings given above in Group 1.

Group 104

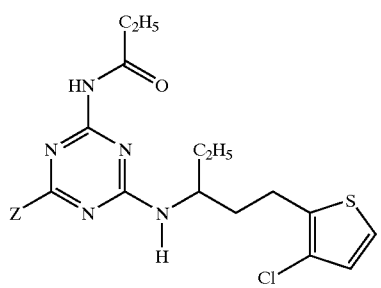

Z has here, for example, the meanings given above in Group 1.

Group 105

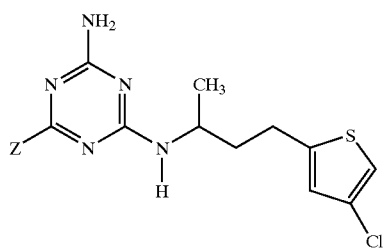

Z has here, for example, the meanings given above in Group 1.

Group 106

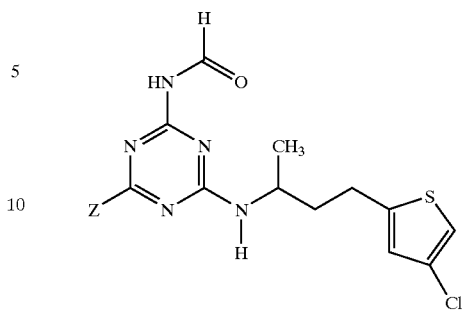

Z has here, for example, the meanings given above in Group 1.

Group 107

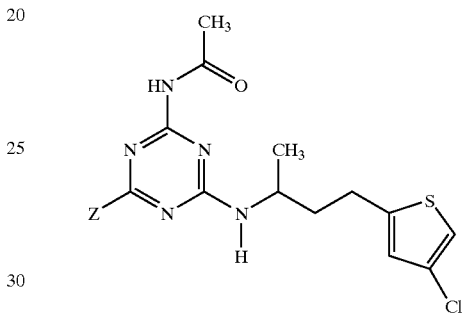

Z has here, for example, the meanings given above in Group 1.

Group 108

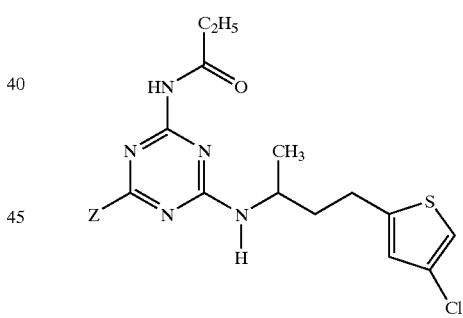

Z has here, for example, the meanings given above in Group 1.

Group 109

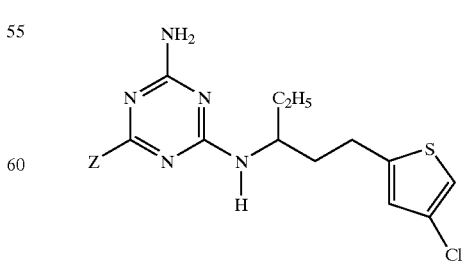

Z has here, for example, the meanings given above in Group 1.

Group 110

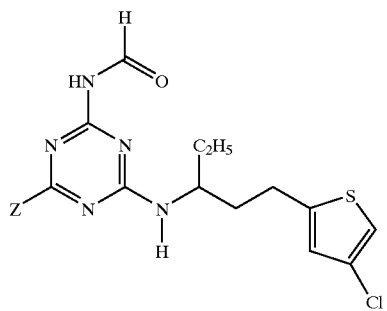

Z has here, for example, the meanings given above in Group 1.

Group 111

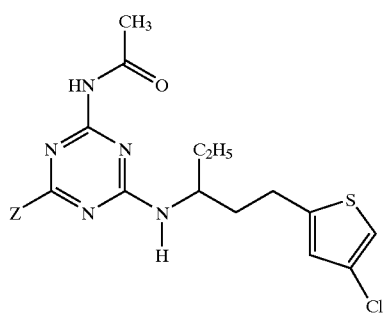

Z has here, for example, the meanings given above in Group 1.

Group 112

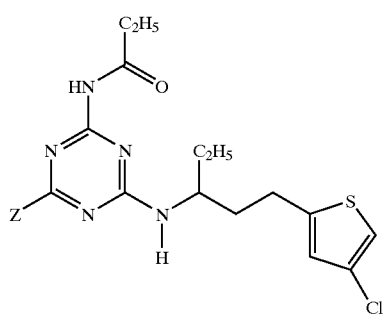

Z has here, for example, the meanings given above in Group 1.

Group 113

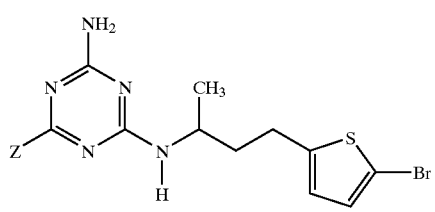

Z has here, for example, the meanings given above in Group 1.

Group 114

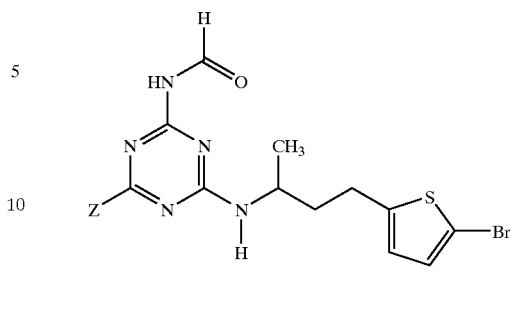

Z has here, for example, the meanings given above in Group 1.

Group 115

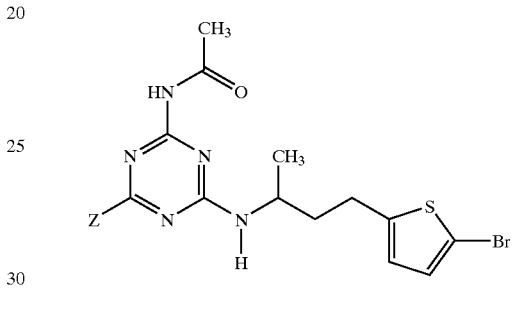

Z has here, for example, the meanings given above in Group 1.

Group 116

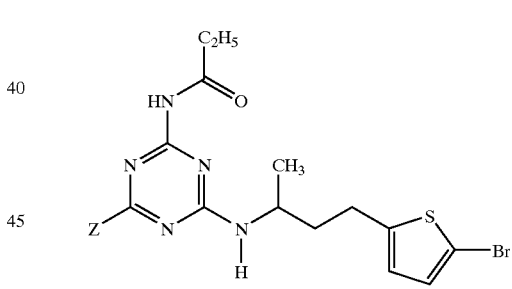

Z has here, for example, the meanings given above in Group 1.

Group 117

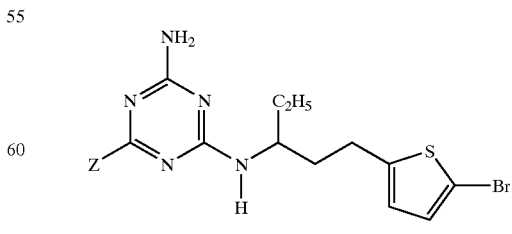

Z has here, for example, the meanings given above in Group 1.

Group 118

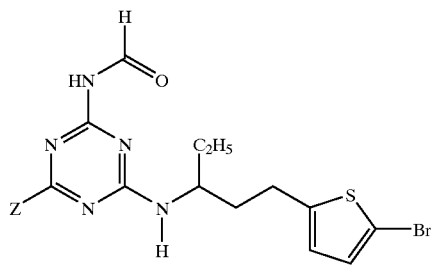

Z has here, for example, the meanings given above in Group 1.

Group 119

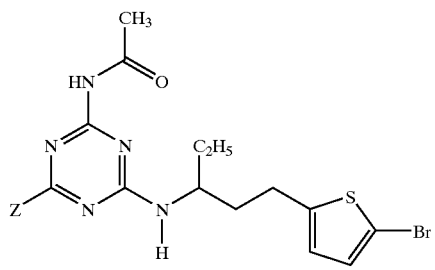

Z has here, for example, the meanings given above in Group 1.

Group 120

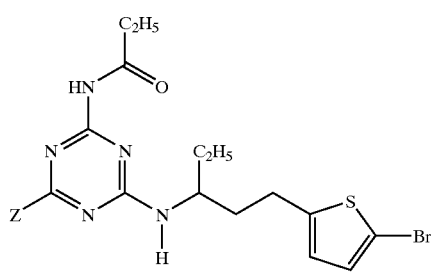

Z has here, for example, the meanings given above in Group 1.

Group 121

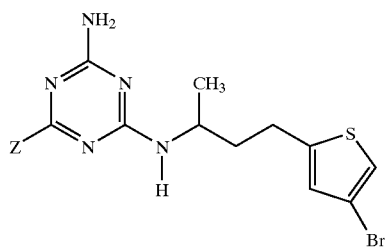

Z has here, for example, the meanings given above in Group 1.

Group 122

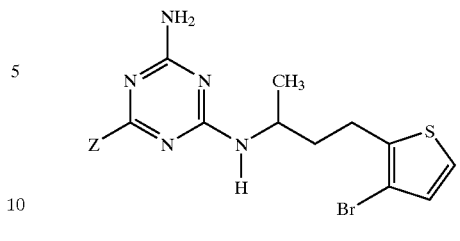

Z has here, for example, the meanings given above in Group 1.

Group 123

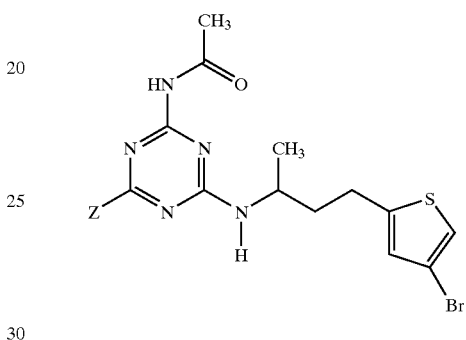

Z has here, for example, the meanings given above in Group 1.

Group 124

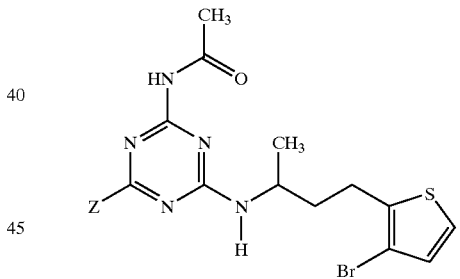

Z has here, for example, the meanings given above in Group 1.

Group 125

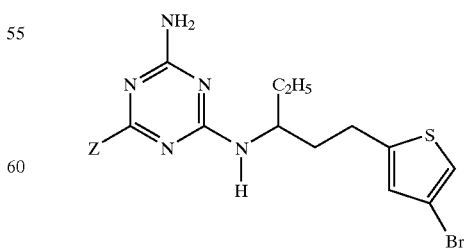

Z has here, for example, the meanings given above in Group 1.

Group 126

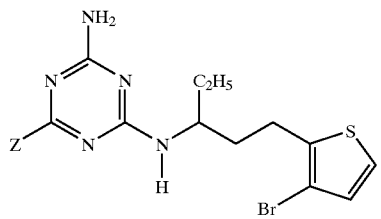

Z has here, for example, the meanings given above in Group 1.

Group 127

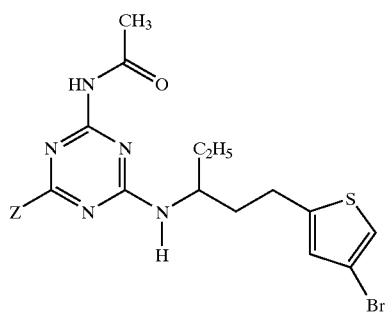

Z has here, for example, the meanings given above in Group 1.

Group 128

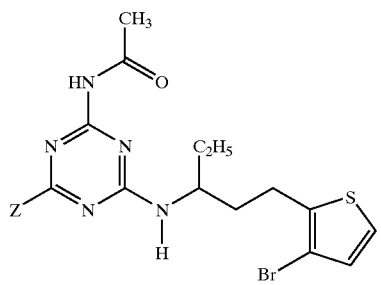

Z has here, for example, the meanings given above in Group 1.

Group 129

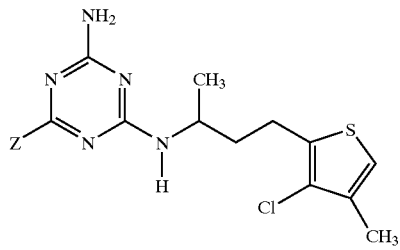

Z has here, for example, the meanings given above in Group 1.

Group 130

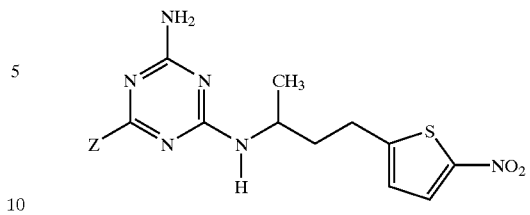

Z has here, for example, the meanings given above in Group 1.

Group 131

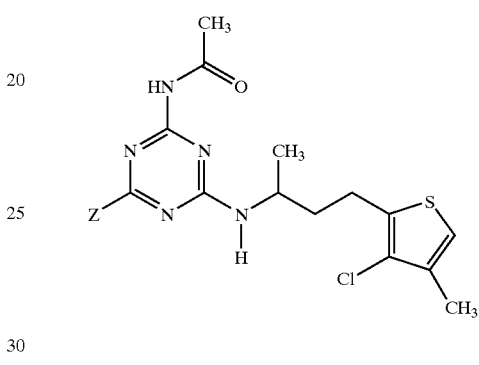

Z has here, for example, the meanings given above in Group 1.

Group 132

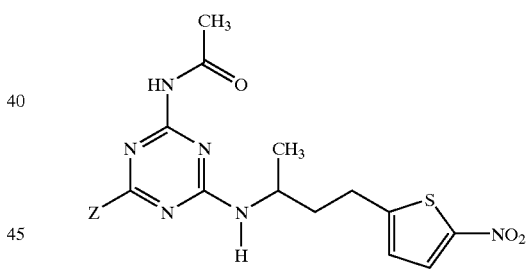

Z has here, for example, the meanings given above in Group 1.

Group 133

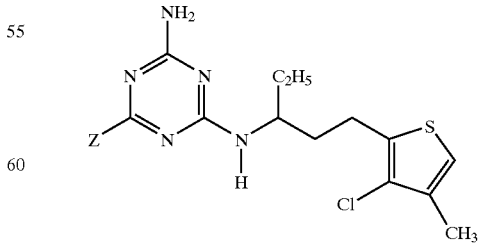

Z has here, for example, the meanings given above in Group 1.

Group 134

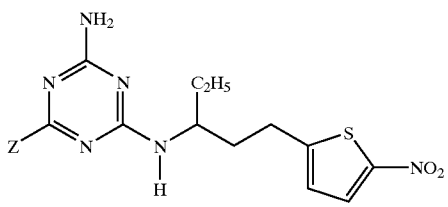

Z has here, for example, the meanings given above in Group 1.

Group 135

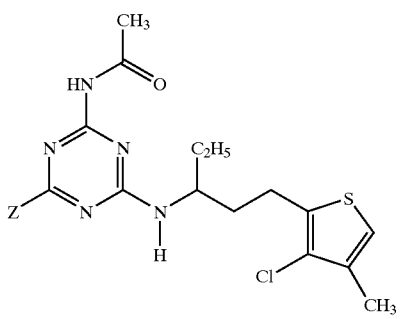

Z has here, for example, the meanings given above in Group 1.

Group 136

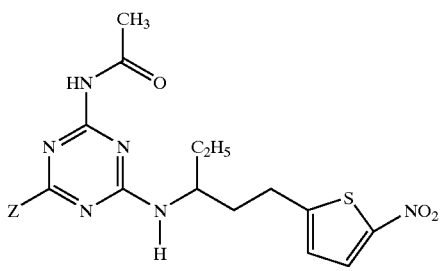

Z has here, for example, the meanings given above in Group 1.

Using, for example, 1-[1-ethyl-4-(thien-2-yl)-butyl]-biguanide and methyl trifluoro-acetate as starting materials, the course of the reaction in the process (a) according to the invention can be illustrated by the following formula scheme:

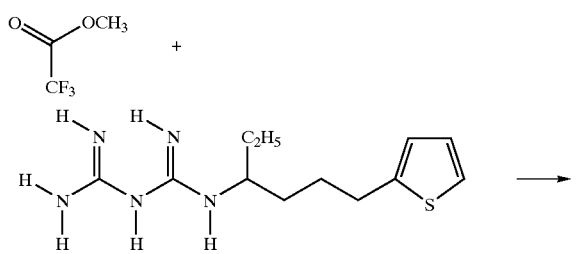

-continued

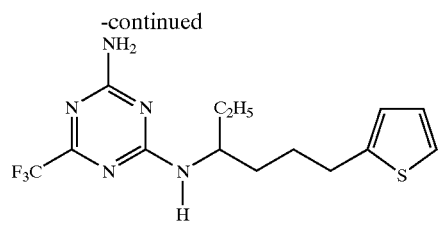

Using, for example, 2-chloro-4-[1-ethyl-4-(2-cyano-thien-3-yl)-propylamino]-6-trifluoromethyl-1,3,5-triazine and ethylamine as starting materials, the course of the reaction in the process (b) according to the invention can be illustrated by the following formula scheme:

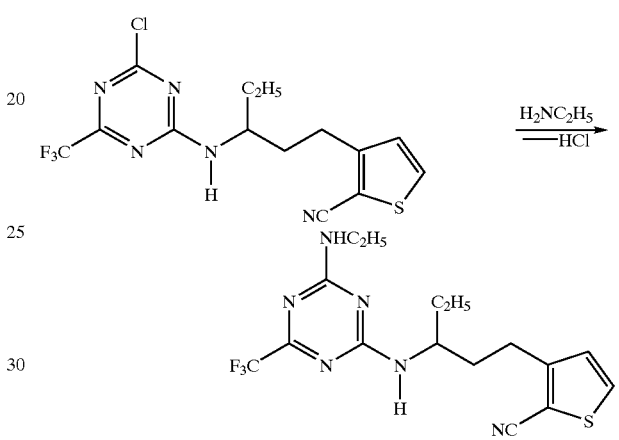

Using, for example, 2-amino-4-methoxy-6-trifluoromethyl-1,3,5-triazine and 1-(3-trifluoromethyl-thien-2-yl)-butane-3-amine as starting materials, the course of the reaction in the process (c) according to the invention can be illustrated by the following formula scheme:

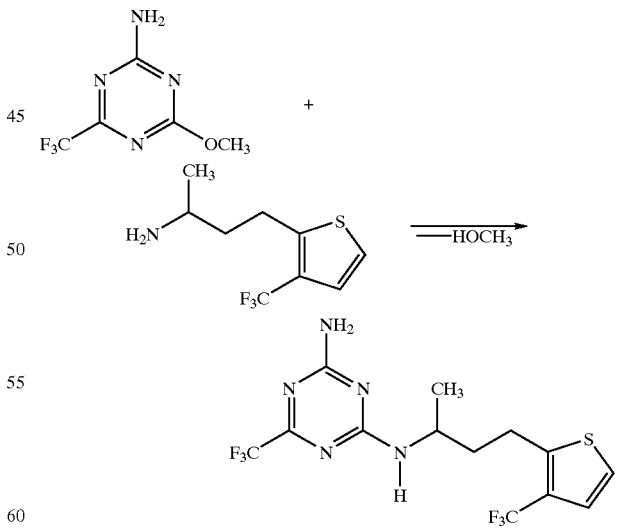

Using, for example, 2-amino-4-[1-ethyl-4-(thien-3-yl)-butylamino]-6-trifluoromethyl-1,3,5-triazine and acetyl chloride as starting materials, the course of the reaction in the process (d) according to the invention can be illustrated by the following formula scheme:

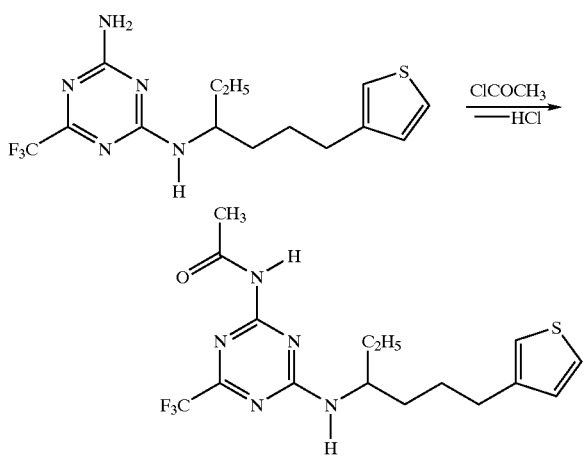

The formula (II) provides a general definition of the biguanides to be used as starting materials in the process (a) according to the invention for preparing compounds of the formula (I). In the formula (II), A, $R^1$, $R^2$, $R^3$, $R^4$ and $R^5$ preferably or in particular have those meanings which have already been mentioned above, in connection with the description of the compounds of the formula (I) according to the invention, as being preferred or as being particularly preferred for A, $R^1$, $R^2$, $R^3$, $R^4$ and $R^5$.

Suitable acid adducts of compounds of the formula (II) are their addition products with protic acids, such as, for example, with hydrogen chloride, hydrogen bromide, sulphuric acid, methanesulphonic acid, benzenesulphonic acid and p-toluenesulphonic acid.

The starting materials of the general formula (II) have hitherto not been disclosed in the literature; as novel substances, they also form part of the subject-matter of the present application.

The novel biguanides of the general formula (II) are obtained when thienylalkylamines of the general formula (VII)

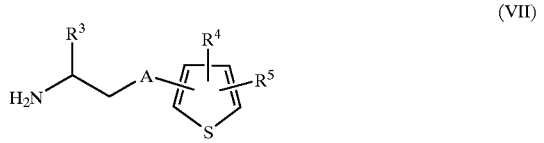

(VII)

in which

A, $R^3$, $R^4$ and $R^5$ are as defined above
and/or acid adducts of compounds of the general formula (VII), such as, for example, the hydrochlorides—are reacted with cyanoguanidine ("dicyandiamide") of the formula (IX)

(IX)

if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf. the Preparation Examples).

After their preparation, the biguanides of the general formula (II) can also be employed directly, without intermediate isolation, for preparing the compounds of the general formula (I) according the process according to the invention (cf. the Preparation Examples)

The thienylalkylamines of the general formula (VII) in which A represents methylene and which are required as intermediates are known and/or can be prepared by processes known per se (cf. EP 94595, EP 101069).

The thienylalkylamines of the general formula (VII) in which A represents dimethylene have hitherto not been disclosed in the literature; as novel substances, they also form part of the subject-matter of the present application.

The novel thienylalkylamines of the general formula (VIIa)

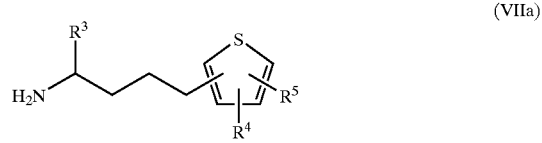

(VIIa)

in which $R^3$, $R^4$ and $R^5$ are as defined above
and/or their acid adducts—are obtained when N-thienylalkyl-formamides of the general formula (X)

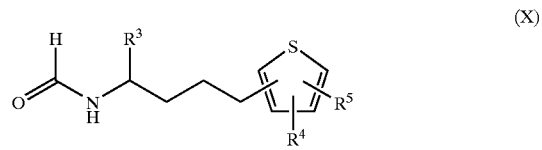

(X)

in which $R^3$, $R^4$ and $R^5$ are as defined above
are heated with acids, such as, for example, hydrochloric acid, in the presence of water to temperatures between 80° C. and 110° C. (cf. the Preparation Examples).

The N-thienylalkyl-formamides of the general formula (X) have hitherto not been disclosed in the literature; as novel substances, they also form part of the subject-matter of the present application.

The novel N-thienylalkyl-formamides of the general formula (X) are obtained when thienylalkyl ketones of the general formula (XI)

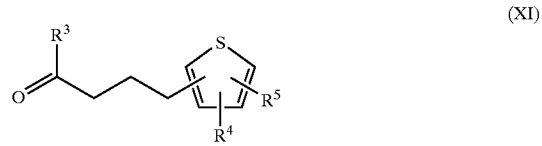

(XI)

in which $R^3$, $R^4$ and $R^5$ are as defined above
are reacted with formamide and formic acid at temperatures between 140° C. and 180° C. (cf. the Preparation Examples).

The thienylalkyl ketones of the general formula (XI) are known and/or can be prepared by processes known per se (cf. Bull. Soc. Chim. France 1954, 1349-1356; Tetrahedron 35 (1979), 329-340).

The formula (III) provides a general definition of the alkoxycarbonyl compounds further to be used as starting materials in the process (a) according to the invention for preparing compounds of the formula (I). In the formula (III), Z preferably or in particular has that meaning which has already been mentioned above, in connection with the description of the compounds of the formula (I) according to the invention, as being preferred or as being particularly preferred for Z; R' preferably represents alkyl having 1 to 4 carbon atoms, in particular methyl or ethyl.

The starting materials of the formula (III) are known chemicals for synthesis.

The formula (IV) provides a general definition of the substituted halogenotriazines to be used as starting materials in the process (b) according to the invention for preparing compounds of the formula (I). In the formula (IV), A, $R^3$, $R^4$, $R^5$ and Z preferably or in particular have those meanings which have already been mentioned above, in connection with the description of the compounds of the formula (I) according to the invention, as being preferred or as being particularly preferred for A, $R^3$, $R^4$, $R^5$ and Z; X preferably represents fluorine or chlorine, in particular chlorine.

The starting materials of the general formula (IV) have hitherto not been disclosed in the literature; as novel substances, they also form part of the subject-matter of the present application.

The substituted halogenotriazines of the general formula (IV) are obtained when the corresponding dihalogenotriazines of the general formula (XII)

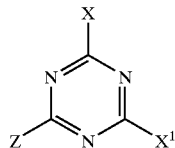

(XII)

in which

X and Z are as defined above and $X^1$ represents halogen (preferably fluorine or chlorine) are reacted with thienylalkylamines of the general formula (VII)

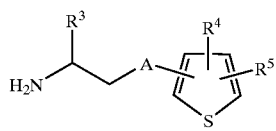

(VII)

in which

A, $R^3$, $R^4$ and $R^5$ are as defined above, if appropriate in the presence of an acid acceptor, such as, for example, ethyl-diisopropylamine, and if appropriate in the presence of a diluent, such as, for example, tetrahydrofuran or dioxane, at temperatures between −50° C. and +50° C.

The formula (VI) provides a general definition of the substituted aminotriazines to be used as starting materials in the process (c) according to the invention for preparing compounds of the formula (I). In the formula (VI), $R^1$, $R^2$ and Z preferably or in particular have those meanings which have already been mentioned above, in connection with the description of the compounds of the formula (I) according to the invention, as being preferred or as being particularly preferred for $R^1$, $R^2$ and Z; $Y^1$ preferably represents fluorine, chlorine, methoxy or ethoxy, in particular chlorine or methoxy.

The starting materials of the general formula (VI) are known and/or can be prepared by processes known per se (cf. WO 95/11237).

The formula (VII) provides a general definition of the thienylalkylamines further to be used as starting materials in the process (c) according to the invention. In the formula (VII), A, $R^3$, $R^4$ and $R^5$ preferably or in particular have those meanings which have already been mentioned above, in connection with the description of the compounds of the formula (I) according to the invention, as being preferred or as being particularly preferred for A, $R^3$, $R^4$ and $R^5$.

The preparation of the starting materials of the general formula (VII) is described above, in the description of the starting materials for the process (a) according to the invention.

The formula (Ia) provides a general definition of the substituted 2,4-diamino-1,3,5-triazines to be used as starting materials in the process (d) according to the invention for preparing pounds of the formula (I). In the formula (Ia), A, $R^1$, $R^3$, $R^4$, $R^5$ and Z preferably in particular have those meanings which have already been mentioned above, in connection with the description of the compounds of the formula (I) according to the invention, as being preferred or as being particularly preferred for A, $R^1$, $R^3$, $R^4$, $R^5$ and Z.

As novel substances, the starting materials of the general formula (Ia) also form part of the subject-matter of the present application; they can be prepared according to the processes (a), (b) or (c) according to the invention (cf. the Preparation Examples).

The formula (VIII) provides a general definition of the alkylating or acylating agents further to be used as starting materials in the process (d) according to the invention. In the formula (VIII), $R^2$ has, with the exception of hydrogen, preferably or in particular that meaning which has already been given above, in connection with the description of the compounds of the formula (I) according to the invention, as being preferred or as being particularly preferred for $R^2$; $Y^2$ preferably represents fluorine, chlorine, bromine, methoxy, ethoxy, acetyloxy or propionyloxy, in particular chlorine, methoxy or acetyloxy.

The starting materials of the general formula (VIII) are known chemicals for synthesis.

The processes according to the invention for preparing the compounds of the formula (I) are, if appropriate, carried out using a reaction auxiliary. Suitable reaction auxiliaries for the processes (a), (b), (c) and (d) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or -i-propoxide, -n-, -i-, -s- or -t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-duisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene or dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a), (b), (c) and (d) according to the invention, the reaction temperatures can be varied within a relatively wide range. In general, the processes are carried out at temperatures between −20° C. and +300° C., preferably between −10° C. and +250° C.

The processes (a), (b), (c) and (d) according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible to use a relatively large excess of in each case one of the components. The reaction is generally carried out in a suitable diluent in the presence of a reaction auxiliary, and the reaction mixture is generally stirred at the required temperature for a plurality of hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuiron, benazolin(-ethyl), benfuresate, bensulfuron(-methyl), bentazone, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-p-methyl), hexazinone, imazamethabenz-(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

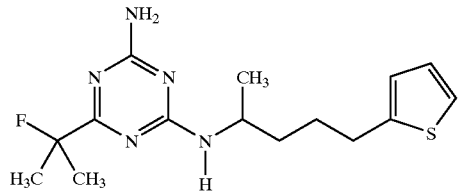

(Process (a) with the Preparation of the Starting Material of the Formula (II))

A mixture of 2.1 g (10 mmol) of 2-amino-5-(thien-2-yl)-pentan hydrochloride and 0.84 g (10 mmol) of cyanoguanidine is heated at 160° C. for 30 minutes. The heating bath is removed and the reaction mixture is then admixed, at about 100° C., with 40 ml of methanol. 2.8 g of molecular sieve are then added and the mixture is cooled to −10° C. and admixed successively with 1.1 g (20 mmol) of sodium methoxide and 1.32 g (11 mmol) of methyl 2-fluoro-isobutyrate. The reaction mixture is stirred at 20° C. for 15 hours. The mixture is then filtered, the filtrate is concentrated under water pump vacuum and the residue is worked up by column chromatography (silica gel, ethyl acetate/hexane, vol. 1:1).

This gives 0.7 g (22% of theory) of 2-amino-4-(1-fluoro-1-methyl-ethyl)-6-(1-methyl-4-(thien-2-yl)-butylamino)-1,3,5-triazine as a pale yellow oil.

Analogously to Example 1, and in accordance with the general description of the preparation processes according to the invention, it is also possible to prepare, for example, the compounds of the formula (I) listed in Table 1 below.

TABLE 1

Examples of the compounds of the formula (I)

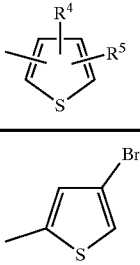

| Ex. No. | A | R¹ | R² | R³ | (thiophene) | Z | Physical data and stereochem. specifications |
|---|---|---|---|---|---|---|---|
| 2 | $CH_2$ | H | H | $C_2H_5$ | 4-Br, 2-methylthiophene | $CF(CH_3)_2$ | (amorphous) (racemate) |
| 3 | $CH_2$ | H | H | $C_2H_5$ | 4-Br, 2-methylthiophene | $CHFCH_3$ | (amorphous) (racemate) |
| 4 | $CH_2$ | H | H | $C_2H_5$ | 5-Br, 2-methylthiophene | $CHFCH_3$ | (amorphous) (racemate) |
| 5 | $CH_2$ | H | H | $C_2H_5$ | 5-Br, 2-methylthiophene | $CF(CH_3)_2$ | (amorphous) (racemate) |
| 6 | $CH_2$ | H | $COCH_3$ | $C_2H_5$ | 4-Br, 2-methylthiophene | $CHFCH_3$ | (amorphous) (racemate) |
| 7 | $CH_2$ | H | $COCH_3$ | $C_2H_5$ | 4-Br, 2-methylthiophene | $CF(CH_3)_2$ | (amorphous) (racemate) |
| 8 | $CH_2$ | H | H | $CH_3$ | 3-methyl, 2-methylthiophene | $CHFCH_3$ | (amorphous) (racemate) |
| 9 | $CH_2$ | H | H | $C_2H_5$ | 3-methyl, 2-methylthiophene | $CHFCH_3$ | (amorphous) (racemate) |
| 10 | $CH_2$ | H | $COCH_3$ | $C_2H_5$ | 3-methyl, 2-methylthiophene | $CHFCH_3$ | (amorphous) (racemate) |

TABLE 1-continued

Examples of the compounds of the formula (I)

| Ex. No. | A | R¹ | R² | R³ | (thiophene with R⁴, R⁵) | Z | Physical data and stereochem. specifications |
|---|---|---|---|---|---|---|---|
| 11 | $CH_2$ | H | $C_2H_5$ C(=O)CH_3 | $C_2H_5$ | 2,3-dimethylthiophene | $CHFCH_3$ | (amorphous) (racemate) |
| 12 | $CH_2$ | H | $CH_3$ C(=O)CH_3 | $CH_3$ | 2,3-dimethylthiophene | $CHFCH_3$ | (amorphous) (racemate) |
| 13 | $CH_2$ | H | $C_2H_5$ C(=O)CH_3 | $CH_3$ | 2,3-dimethylthiophene | $CHFCH_3$ | (amorphous) (racemate) |
| 14 | $CH_2$ | H | H | $C_2H_5$ | 2,5-dichloro-3-methylthiophene | $CHFCH_3$ | (amorphous) (racemate) |
| 15 | $CH_2$ | H | H | $C_2H_5$ | 2,5-dichloro-3-methylthiophene | $CF(CH_3)_2$ | (amorphous) (racemate) |
| 16 | $CH_2$ | H | H | $C_2H_5$ | 2,5-dichloro-3-methylthiophene | $CH_3$ | (amorphous) (racemate) |
| 17 | $CH_2$ | H | H | $C_2H_5$ | 2,5-dichloro-3-methylthiophene | $CHClCH_3$ | (amorphous) (racemate) |
| 18 | $CH_2$ | H | $CH_3$ C(=O)CH_3 | $C_2H_5$ | 2,5-dichloro-3-methylthiophene | $CF(CH_3)_2$ | (amorphous) (racemate) |
| 19 | $CH_2$ | H | H | $C_2H_5$ | 3-bromo-2-methylthiophene | $CF(CH_3)_2$ | (amorphous) (racemate) |

TABLE 1-continued

Examples of the compounds of the formula (I)

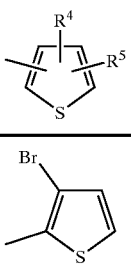

| Ex. No. | A | R¹ | R² | R³ | (thiophene with R⁴, R⁵) | Z | Physical data and stereochem. specifications |
|---|---|---|---|---|---|---|---|
| 20 | $CH_2$ | H | H | $C_2H_5$ | 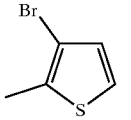 | $CHFCH_3$ | (amorphous) (racemate) |
| 21 | $CH_2$ | H | H | $C_2H_5$ | 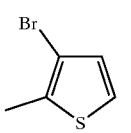 | $CH_3$ | (amorphous) (racemate) |
| 22 | $CH_2$ | H | $\underset{O}{\overset{CH_3}{\text{C}}}$ | $C_2H_5$ | 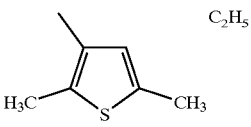 | $CHFCH_3$ | (amorphous) (racemate) |
| 23 | $CH_2$ | H | H | $C_2H_5$ | 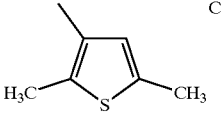 | $C_2H_5$ | (amorphous) (racemate) |
| 24 | $CH_2$ | H | H | $C_2H_5$ | 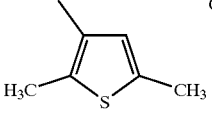 | $CF(CH_3)_2$ | (amorphous) (racemate) |
| 25 | $CH_2$ | H | H | $C_2H_5$ | 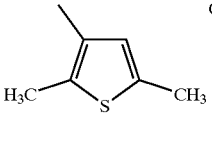 | $CHFCH_3$ | (amorphous) (racemate) |
| 26 | $CH_2$ | H | $\underset{O}{\overset{CH_3}{\text{C}}}$ | $C_2H_5$ | 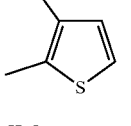 | $CF(CH_3)_2$ | (amorphous) (racemate) |
| 27 | $CH_2$ | H | H | $C_2H_5$ | 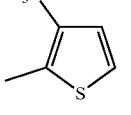 | $CF(CH_3)_2$ | (amorphous) (racemate) |
| 28 | $CH_2$ | H | H | $C_2H_5$ | (same thiophene as 27) | $CHF_3$ | (amorphous) (racemate) |

TABLE 1-continued

Examples of the compounds of the formula (I)

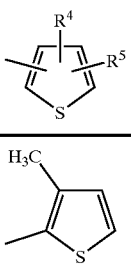

| Ex. No. | A | $R^1$ | $R^2$ | $R^3$ | 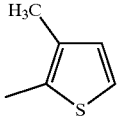 | Z | Physical data and stereochem. specifications |
|---|---|---|---|---|---|---|---|
| 29 | $CH_2$ | H | H | $C_2H_5$ | 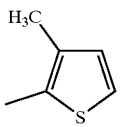 | $CHFCH_3$ | (amorphous) (racemate) |
| 30 | $CH_2$ | H | H | $C_2H_5$ | 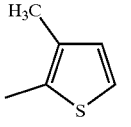 | $CH_2OCH_3$ | (amorphous) (racemate) |
| 31 | $CH_2$ | H | H | $C_2H_5$ | 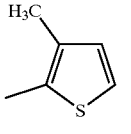 | $CF_3$ | (amorphous) (racemate) |
| 32 | $CH_2$ | H | H | $C_2H_5$ | | $CF_2Cl$ | (amorphous) (racemate) |
| 33 | $CH_2$ | H | H | $C_2H_5$ | 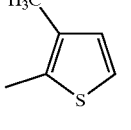 | $CHCl_2$ | (amorphous) (racemate) |
| 34 | $CH_2$ | H | H | $C_2H_5$ | 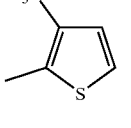 | $CF_2CF_3$ | (amorphous) (racemate) |
| 35 | $CH_2$ | H | H | $C_2H_5$ | 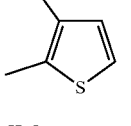 | $CBr(CH_3)_2$ | (amorphous) (racemate) |
| 36 | $CH_2$ | H | H | $C_2H_5$ | | $(CH_2)_2OCH_3$ | (amorphous) (racemate) |
| 37 | $CH_2$ | H | H | $C_2H_5$ | 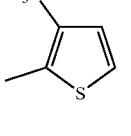 | $CF_2Br$ | (amorphous) (racemate) |

TABLE 1-continued

Examples of the compounds of the formula (I)

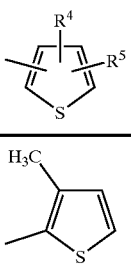

| Ex. No. | A | $R^1$ | $R^2$ | $R^3$ | 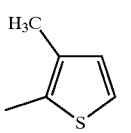 | Z | Physical data and stereochem. specifications |
|---|---|---|---|---|---|---|---|
| 38 | $CH_2$ | H | H | $CH_3$ | 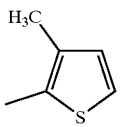 | $CF_3$ | (amorphous) (racemate) |
| 39 | $CH_2$ | H | H | $CH_3$ | 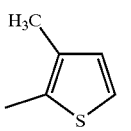 | $CHF_2$ | (amorphous) (racemate) |
| 40 | $CH_2$ | H | H | $CH_3$ | 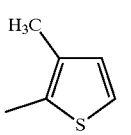 | $CHCl_2$ | (amorphous) (racemate) |
| 41 | $CH_2$ | H | H | $CH_3$ | 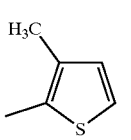 | $CF_2Cl$ | (amorphous) (racemate) |
| 42 | $CH_2$ | H | H | $CH_3$ | 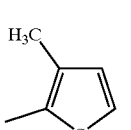 | $CF_2CF_3$ | (amorphous) (racemate) |
| 43 | $CH_2$ | H | H | $CH_3$ | 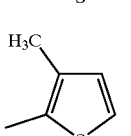 | $CHClCH_3$ | (amorphous) (racemate) |
| 44 | $CH_2$ | H | H | $CH_3$ | | $CH_3$ | (amorphous) (racemate) |
| 45 | $CH_2$ | H | H | $CH_3$ | | $C_2H_5$ | (amorphous) (racemate) |
| 46 | $CH_2$ | H | H | $CH_3$ | 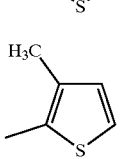 | $CH(CH_3)_2$ | (amorphous) (racemate) |

TABLE 1-continued

Examples of the compounds of the formula (I)

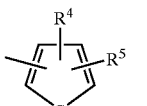

| Ex. No. | A | $R^1$ | $R^2$ | $R^3$ | 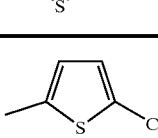 | Z | Physical data and stereochem. specifications |
|---|---|---|---|---|---|---|---|
| 47 | $CH_2$ | H | H | $CH_3$ | 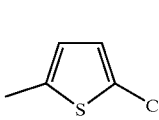 | $CHFCH_3$ | (amorphous) (racemate) |
| 48 | $CH_2$ | H | H | $C_2H_5$ | 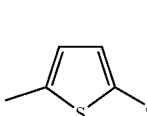 | $CHFCH_3$ | (amorphous) (racemate) |
| 49 | $CH_2$ | H | H | $C_2H_5$ | 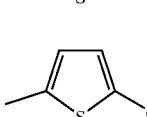 | $CF(CH_3)_2$ | (amorphous) (racemate) |
| 50 | $CH_2$ | H | H | $C_2H_5$ | 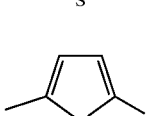 | $CF_3$ | (amorphous) (racemate) |
| 51 | $CH_2$ | H | H | $C_2H_5$ | 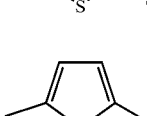 | $CH_2OCH_3$ | (amorphous) (racemate) |
| 52 | $CH_2$ | H | H | $C_2H_5$ | 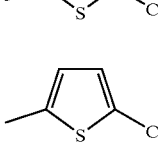 | $CHCl_2$ | (amorphous) (racemate) |
| 53 | $CH_2$ | H | H | $CH_3$ |  | $CF(CH_3)_2$ | (amorphous) (racemate) |
| 54 | $CH_2$ | H | H | $CH_3$ | 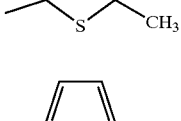 | $CH_2OCH_3$ | (amorphous) (racemate) |
| 55 | $CH_2$ | H | H | $CH_3$ |  | $CHCl_2$ | (amorphous) (racemate) |
| 56 | $CH_2$ | H | H | $CH_3$ | | $CF_3$ | (amorphous) (racemate) |

Starting Materials of the Formula (VII)

Example (VII-1)

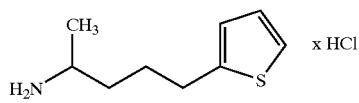

A mixture of 9.8 g (50 mmol) of N-(1-methyl-4-(thien-2-yl)-butyl)-formamide, 100 ml of conc. hydrochloric acid and 40 ml of water is heated under reflux for 90 minutes. The mixture is then concentrated substantially under water pump vacuum, and the residue is stirred with diethyl ether. The ether phase is decanted off and the solvent is carefully distilled off from the residue under water pump vacuum.

This gives 8.5 g (83% of theory) of 2-amino-5-(thien-2-yl)-pentane hydrochloride as a dark oil.

Starting Materials of the Formula (X)

Example (X-1)

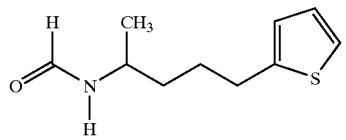

A mixture of 10.2 g (60 mmol) of 5-(thien-2-yl)-pentan-2-one and 60 ml of formamide is heated to from 150° C. to 160° C. and, after addition of 13.5 g of formic acid, stirred at 160° C. for 2 hours. After cooling to room temperature (about 20° C.), the reaction mixture is stirred with toluene/water and the organic phase is separated off, dried with sodium sulphate and filtered. From the filtrate, the solvent is carefully distilled off under reduced pressure (finally 2 mbar at 80° C.).

This gives 9.8 g (83% of theory) of N-(1-methyl-4-(thien-2-yl)-butyl)-formamide as an oily residue.

Use Examples

Example A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liters of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Example 1, 4, 5, 6, 7, 19, 20, 22, 25 and 26 exhibit strong activity against weeds and are largely tolerated well by crop plants, such as, for example, cotton, maize, wheat and barley.

Example B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Example 1, 2, 4, 5, 6 and 7 exhibit strong activity against weeds and are tolerated well by crop plants, such as, for example, maize, barley and wheat.

TABLE A

| | Pre-emergence test/greenhouse | | | | | |
|---|---|---|---|---|---|---|
| Active compound according to Preparation Example No. according to the invention: | Application rate (g of ai./ha) | maize | Alopecurus | Amaranthus | Sinapis | wheat |
| (structure) | 1000 | 0 | 80 | 95 | 90 | |

TABLE A-continued

Pre-emergence test/greenhouse

| Structure | | | |
|---|---|---|---|
| [triazine with NH2, CHF-CH3, NH-CH(C2H5)-CH2CH2-(5-Br-thiophene)] | 500 | 0 | 0 |
| [triazine with NH2, C(CH3)2F, NH-CH(C2H5)-CH2CH2-(5-Br-thiophene)] | 500 | 0 | 0 |
| [triazine with NHCOCH3, CHF-CH3, NH-CH(C2H5)-CH2CH2-(4-Br-thiophene)] | 500 | 0 | |
| [triazine with NHCOCH3, C(CH3)2F, NH-CH(C2H5)-CH2CH2-(4-Br-thiophene)] | 500 | 95 | 0 |
| [triazine with NH2, C(CH3)2F, NH-CH(C2H5)-CH2CH2-(3-Br-thiophene)] | 500 | 100 | |
| [triazine with NH2, CHF-CH3, NH-CH(C2H5)-CH2CH2-(3-Br-thiophene)] | 500 | 100 | |

TABLE A-continued
Pre-emergence test/greenhouse
| | | | | |
|---|---|---|---|---|
| 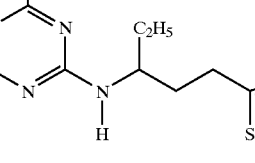 | 500 | | 100 | 0 |
| 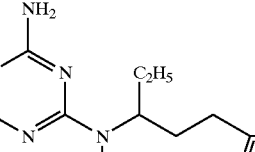 | 500 | 0 | 100 | 0 |
| 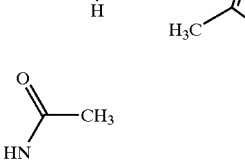 | 500 | 0 | | 0 |
| Active compound according to Preparation Example No. according to the invention: | Application rate (g of ai./ha) | Digitaria | Chenopodium | Solanum | Veronica |
|---|---|---|---|---|---|
| 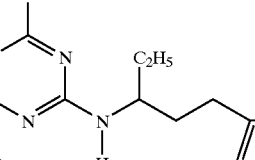 | 1000 | | | | |
| 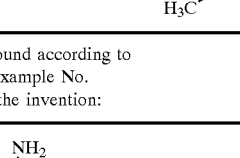 | 500 | 100 | 100 | 100 | 100 |
| 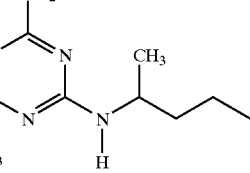 | 500 | 100 | 100 | 100 | 100 |

TABLE A-continued

Pre-emergence test/greenhouse

| Structure | | | | | |
|---|---|---|---|---|---|
| (F-CH(CH₃)-triazine-NHAc, NH-CH(C₂H₅)-CH₂CH₂-(4-Br-thienyl)) | 500 | 100 | | | 100 |
| (tBu-triazine-NHAc, NH-CH(C₂H₅)-CH₂CH₂-(4-Br-thienyl)) | 500 | 100 | 100 | 100 | 100 |
| (tBu-triazine-NH₂, NH-CH(C₂H₅)-CH₂CH₂-(3-Br-thienyl)) | 500 | | | | 100 |
| (F-CH(CH₃)-triazine-NH₂, NH-CH(C₂H₅)-CH₂CH₂-(3-Br-thienyl)) | 500 | 100 | | 100 | 100 |
| (F-CH(CH₃)-triazine-NHAc, NH-CH(C₂H₅)-CH₂CH₂-(3-Br-thienyl)) | 500 | | | 100 | 100 |
| (F-CH(CH₃)-triazine-NH₂, NH-CH(C₂H₅)-CH₂CH₂-(2,5-diMe-thienyl)) | 500 | 100 | | 100 | 100 |

TABLE A-continued

Pre-emergence test/greenhouse

| Active compound according to Preparation Example No. according to the invention: | Application rate (g of ai./ha) | Viola | barley | Setaria | Cyperus | Matricaria |
|---|---|---|---|---|---|---|
| [structure: triazine with NHC(O)CH₃, CF(CH₃)₂, and NH-CH(C₂H₅)-CH₂CH₂-(2,5-dimethylthiophene)] | 500 | | 100 | | | |
| [structure: triazine with NH₂, CF(CH₃)₂, and NH-CH(CH₃)-CH₂CH₂CH₂-thiophene] | 1000 | 100 | | | | |
| [structure: triazine with NH₂, CHF(CH₃), and NH-CH(C₂H₅)-CH₂CH₂-(5-bromothiophene)] | 500 | 100 | | | | |
| [structure: triazine with NH₂, CF(CH₃)₂, and NH-CH(C₂H₅)-CH₂CH₂-(5-bromothiophene)] | 500 | 100 | | | | |
| [structure: triazine with NHC(O)CH₃, CHF(CH₃), and NH-CH(C₂H₅)-CH₂CH₂-(4-bromothiophene)] | 500 | 100 | 0 | 95 | | |

TABLE A-continued

Pre-emergence test/greenhouse

| Structure | | | |
|---|---|---|---|
| (acetamido-triazine with tert-butyl-F, C₂H₅, 4-bromothiophene) | 500 | 100 | 95 |
| (amino-triazine with tert-butyl-F, C₂H₅, 3-bromothiophene) | 500 | 100 | 100 |
| (amino-triazine with CHF-CH₃, C₂H₅, 3-bromothiophene) | 500 | | |
| (acetamido-triazine with CHF-CH₃, C₂H₅, 3-bromothiophene) | 500 | | 100 |
| (amino-triazine with CHF-CH₃, C₂H₅, 2,5-dimethylthiophene) | 500 | 100 | |

TABLE A-continued

Pre-emergence test/greenhouse

| Active compound according to Preparation Example No. according to the invention: | Application rate (g of ai./ha) | cotton | Datura | soya | Lolium |
|---|---|---|---|---|---|
| [structure] | 500 | 100 | | | 95 |
| [structure] | 1000 | | | | |
| [structure] | 500 | | | | |
| [structure] | 500 | | | | |
| [structure] | 500 | | | | |

TABLE A-continued

Pre-emergence test/greenhouse

| Structure | | | |
|---|---|---|---|
| [triazine with NHC(O)CH₃, C(CH₃)₂F, NH-CH(C₂H₅)-CH₂CH₂-(4-bromothien-2-yl)] | 500 | | |
| [triazine with NH₂, C(CH₃)₂F, NH-CH(C₂H₅)-CH₂CH₂-(3-bromothien-2-yl)] | 500 | | |
| [triazine with NH₂, CH(CH₃)F, NH-CH(C₂H₅)-CH₂CH₂-(3-bromothien-2-yl)] | 500 | 0 | 100 |
| [triazine with NHC(O)CH₃, CH(CH₃)F, NH-CH(C₂H₅)-CH₂CH₂-(3-bromothien-2-yl)] | 500 | 0 | |
| [triazine with NH₂, CH(CH₃)F, NH-CH(C₂H₅)-CH₂CH₂-(2,5-dimethylthien-3-yl)] | 500 | | 0 |
| [triazine with NHC(O)CH₃, C(CH₃)₂F, NH-CH(C₂H₅)-CH₂CH₂-(2,5-dimethylthien-3-yl)] | 500 | | 90 |

TABLE B

Post-emergence test/greenhouse

| Active compound according to Preparation Example No. | Application rate (g of ai./ha) | maize | Setaria | Abutilon | Amaranthus | Sinapis |
|---|---|---|---|---|---|---|
| according to the invention: 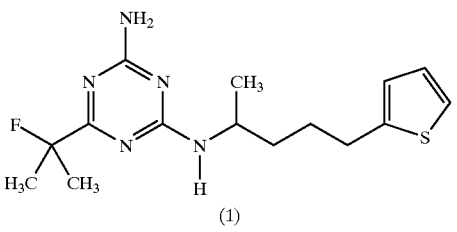 (1) | 1000 | 30 | 80 | 95 | 100 | 100 |

| Active compound according to Preparation Example No. | Application rate (g of ai./ha) | barley | wheat | Datura | Ipomoea | Solanum | Viola |
|---|---|---|---|---|---|---|---|
| according to the invention: 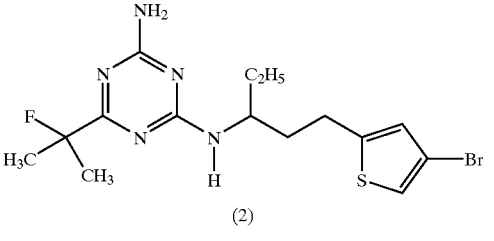 (2) | 125 | 0 | 0 | 95 | 95 | 100 | 95 |
| 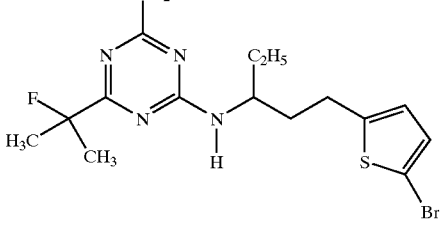 (5) | 500 | 0 | 0 | 100 | 95 | 100 | 95 |

| Active compound according to Preparation Example No. | Application rate (g of ai./ha) | barley | wheat | Datura | Ipomoea | Solanum | Viola |
|---|---|---|---|---|---|---|---|
| 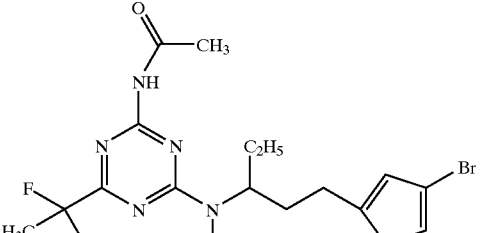 (7) | 500 | 0 | 0 | 100 | 100 | 100 | 100 |

TABLE B

| | Post-emergence test/greenhouse | | | | | | | |
|---|---|---|---|---|---|---|---|---|
| Active compound according to Preparation Example No. | Application rate (g of ai./ha) | barley | wheat | Setaria | Datura | Ipomoea | Solanum | Viola |
| according to the invention: 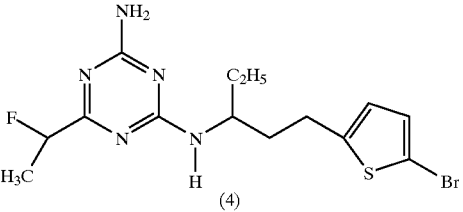 (4) | 500 | 0 | 0 | 80 | 95 | 95 | 95 | 100 |

| Active compound according to Preparation Example No. | Application rate (g of ai./ha) | barley | wheat | digitaria | Datura | Ipomoea | Solanum | Viola |
|---|---|---|---|---|---|---|---|---|
| according to the invention: 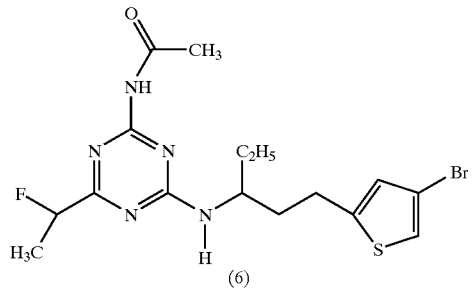 (6) | 500 | 0 | 0 | 90 | 100 | 100 | 100 | 100 |

What is claimed is:

1. A thienylalkylamino-1,3,5-triazine of the formula (I)

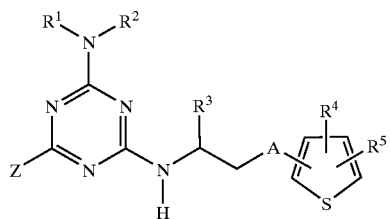

wherein
A represents methylene (—$CH_2$—) or dimethylene (—$CH_2CH_2$—),
$R^1$ represents hydrogen or represents optionally cyano-, halogen- or $C_1$–$C_4$-alkoxy-substituted alkyl having 1 to 4 carbon atoms,
$R^2$ represents hydrogen, represents formyl or represents optionally cyano-, halogen- or $C_1$–$C_4$-alkoxy-substituted alkyl, alkylcarbonyl, alkoxycarbonyl or alkylaminocarbonyl having 1 to 4 carbon atoms in the alkyl groups,
$R^3$ represents optionally cyano-, halogen- or $C_1$–$C_4$-alkoxy-substituted alkyl having 1 to 4 carbon atoms or represents optionally cyano-, halogen- or $C_1$–$C_4$-alkyl-substituted cycloalkyl having 3 to 6 carbon atoms,
$R^4$ represents nitro, cyano, carbamoyl, thiocarbamoyl, halogen, represents optionally halogen-substituted alkyl, alkoxy, alkylcarbonyl or alkoxycarbonyl having up to 4 carbon atoms, or where A represents dimethylene also represents hydrogen,
$R^5$ represents hydrogen, halogen or represents optionally halogen-substituted alkyl or alkoxy having 1 to 4 carbon atoms, and
Z represents hydrogen, represents optionally cyano-, halogen-, hydroxyl-, $C_1$–$C_4$-alkoxy- or $C_1$–$C_4$-alkylthio-substituted alkyl having 1 to 6 carbon atoms, represents optionally cyano-, halogen- or $C_1$–$C_4$-alkoxy-substituted alkoxycarbonyl, alkylsulphinyl or alkylsulphonyl having 1 to 6 carbon atoms in the alkyl groups, represents optionally halogen-substituted alkenyl or alkenyl having 2 to 6 carbon atoms, or represents optionally cyano-, halogen- or $C_1$–$C_4$ alkyl-substituted cycloalkyl having 3 to 6 carbon atoms.

2. The thienylalkylamino-1,3,5-triazine of claim 1, wherein
A represents methylene (—$CH_2$—) or dimethylene (—$CH_2CH_2$—),
$R^1$ represents hydrogen or represents optionally cyano-, fluorine-, chlorine-, methoxy- or ethoxy-substituted methyl, ethyl, n- or i-propyl,
$R^2$ represents hydrogen, represents formyl or represents optionally cyano-, fluorine-, chlorine-, methoxy- or ethoxy-substituted methyl, ethyl, n- or i-propyl, acetyl, propionyl, n- or i-butyroyl, methoxycarbonyl, ethoxycarbonyl, n- or i-propoxycarbonyl, methylaminocarbonyl, ethyl-aminocarbonyl, n- or i-propylaminocarbonyl,
$R^3$ represents optionally cyano-, fluorine-, chlorine-, methoxy- or ethoxy-substituted methyl, ethyl, n- or i-propyl, or represents optionally cyano-, fluorine-, chlorine-, methyl- or ethyl-substituted cyclopropyl, cyclobutyl, cyclopentyl or cyclohexyl, R⁴ represents nitro, cyano, carbamoyl, thiocarbamoyl, fluorine, chlorine, bromine, or represents optionally fluorine- and/or chlorine-substituted methyl, ethyl, n- or i-propyl, methoxy, ethoxy, n- or i-propoxy and where A represents dimethylene also represents hydrogen, R⁵ represents hydrogen, fluorine, chlorine, bromine, or represents optionally fluorine- and/or chlorine-substituted methyl, ethyl, n- or i-propyl, methoxy, ethoxy, n- or i-propoxy, and Z represents hydrogen, represents optionally cyano-, fluorine-, chlorine-, bromine-, hydroxyl-, methoxy-, ethoxy-, methylthio- or ethylthio-substituted methyl, ethyl, n- or i-propyl, n-, i-, s- or t-butyl, represents optionally cyano-, fluorine-, chlorine-, methoxy- or ethoxy-substituted methoxycarbonyl, ethoxycarbonyl, n- or i-propoxycarbonyl, methyl-sulphinyl, ethylsulphinyl, n- or i-propylsulphinyl, methylsulphonyl, ethyl-sulphonyl, n- or i-propylsulphonyl, represents optionally fluorine-, chlorine- and/or bromine-substituted ethenyl, propenyl butenyl, ethinyl, propinyl or butinyl, or represents optionally cyano-, fluorine-, chlorine-, bromine-, methyl- or ethyl-substituted cyclopropyl, cyclobutyl, cyclo-pentyl or cyclohexyl.

3. A thienylalkylamino-1,3,5-triazine of the formula (I) according to claim 1, wherein A represents methylene (—CH₂—) or dimethylene (—CH₂CH₂—), R¹ represents hydrogen, R² represents hydrogen, formyl, acetyl, propionyl, n- or i-butyroyl, methoxycarbonyl, ethoxycarbonyl, n- or i-propoxycarbonyl, R³ represents methyl, ethyl, n- or i-propyl, R⁴ represents nitro, cyano, fluorine, chlorine, bromine, or represents in each case optionally fluorine- and/or chlorine-substituted methyl, ethyl, n- or i-propyl, methoxy, ethoxy, n- or i-propoxy and—in the case that A represents dimethylene—also represents hydrogen, R⁵ represents hydrogen, fluorine, chlorine, bromine, or represents in each case optionally fluorine- and/or chlorine-substituted methyl, ethyl, n- or i-propyl, methoxy, ethoxy, n- or i-propoxy, and Z represents optionally fluorine-, chlorine-, methoxy- or ethoxy-substituted methyl, ethyl, n- or i-propyl, or represents cyclo-propyl.

4. A process for preparing the thienylalkylamino-1,3,5-triazines of the formula (I)

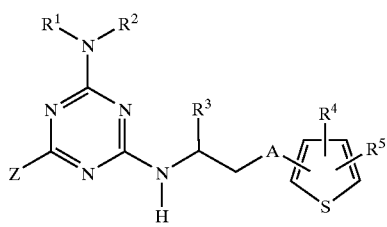

in which

A, R¹, R², R³, R⁴, R⁵ and Z are as defined in claim 1, comprising the step of reacting a biguanide of the formula (II)

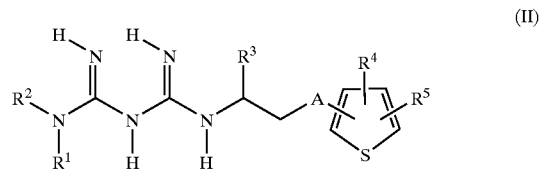

in which

A, R¹, R², R³, R⁴ and R⁵ are as defined above and/or acid adducts of compounds of the formula (II)—with an alkoxycarbonyl compound of the formula (III)

in which

Z is as defined above and

R' represents alkyl.

5. A herbicidal composition, comprising a thienylalkylamino-1,3,5-triazine according to claim 1 and an inert carrier.

6. A method for controlling undesirable plants, comprising the step of applying an effective amount of a thienylalkylamino-1,3,5-triazine according to claim 1 to undesirable plants and/or their habitat.

7. A thienylalkylamino-1,3,5-triazine according to claim 1, wherein R³ represents methyl, ethyl, n- or i-propyl.

8. A thienylalkylamino-1,3,5-triazine according to claim 1, Z represents optionally fluorine-, chlorine-, methoxy- or ethoxy-substituted methyl, ethyl, n- or i-propyl, or represents cyclopropyl.

9. A thienylalkylamino-1,3,5-triazine of the formula (I)

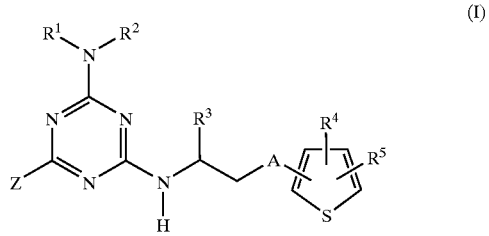

wherein

A represents methylene (—CH₂—) or dimethylene (—CH₂CH₂—),

R¹ represents hydrogen or represents optionally cyano-, halogen- or C₁–C₄-alkoxy-substituted alkyl having 1 to 4 carbon atoms, R² represents hydrogen, represents formyl or represents optionally cyano-, halogen- or C₁–C₄-alkoxy-substituted alkyl, alkylcarbonyl, alkoxycarbonyl or alkylaminocarbonyl having 1 to 4 carbon atoms in the alkyl groups, R³ represents optionally cyano-, halogen- or C₁–C₄-alkoxy-substituted alkyl having 1 to 4 carbon atoms or represents optionally cyano-, halogen- or C₁–C₄-alkyl-substituted cycloalkyl having 3 to 6 carbon atoms, R⁴ represents nitro, cyano, carbamoyl, thiocarbamoyl, halogen, represents optionally halogen-substituted alkyl, alkoxy, alkylcarbonyl or alkoxycarbonyl having up to 4 carbon atoms, or where A represents dimethylene also represents hydrogen, R⁵ represents hydrogen, halogen or represents optionally halogen-substituted alkyl or alkoxy having 1 to 4 carbon atoms, and Z represents hydrogen, or represents halogen, or represents optionally cyano-, halogen-, hydroxyl-, $C_1$–$C_4$-alkoxy- or $C_1$–$C_4$-alkylthio-substituted alkyl or alkoxy having 1 to 6 carbon atoms, or represents optionally halogen-substituted alkenyl or alkenyl having 2 to 6 carbon atoms, or represents optionally cyano-, halogen- or $C_1$–$C_4$-alkyl-substituted cycloalkyl having 3 to 6 carbon atoms.

10. A thienylalkylamino-1,3,5-triazine according to claim 9, wherein Z represents optionally cyano-, halogen-, hydroxyl-, $C_1$–$C_4$-alkoxy- or $C_1$–$C_4$-alkylthio-substituted alkyl having in each case 1 to 6 carbon atoms, represents cyano-substituted alkoxy having in each case 1 to 6 carbon atoms, or represents optionally cyano-, halogen- or $C_1$–$C_4$-alkyl-substituted cycloalkyl having 3 to 6 carbon atoms.

11. A thienylalkylamino-1,3,5-triazine according to claim 8, wherein Z represents optionally fluorine-, chlorine-, methoxy- or ethoxy-substituted methyl, ethyl, n- or i-propyl, or represents cyclopropyl.

12. A thienylalkylamino-1,3,5-triazine according to claim 1, wherein the thienyl-alkylamino-1,3,5-triazine is a racemate.

13. A thienylalkylamino-1,3,5-triazine according to claim 9, wherein the thienyl-alkylamino-1,3,5-triazine is a racemate.

* * * * *